United States Patent [19]

Wiegand et al.

[11] Patent Number: 5,686,592
[45] Date of Patent: Nov. 11, 1997

[54] HIGH-AFFINITY OLIGONUCLEOTIDE LIGANDS TO IMMUNOGLOBULIN E (IGE)

[75] Inventors: Torsten Walter Wiegand; Diane Tasset; Larry Gold, all of Boulder, Colo.

[73] Assignee: NeXstar Pharmaceuticals, Inc., Boulder, Colo.

[21] Appl. No.: 471,985

[22] Filed: Jun. 6, 1995

Related U.S. Application Data

[63] Continuation-in-part of Ser. No. 714,131, Jun. 10, 1991, Pat. No. 5,475,096, which is a continuation-in-part of Ser. No. 536,428, Jun. 11, 1990, abandoned, and Ser. No. 964,624, Oct. 21, 1992, Pat. No. 5,496,938, and Ser. No. 317,403, Oct. 3, 1994.

[51] Int. Cl.⁶ .................. C07H 21/04; C07H 21/02; C12P 19/34; C12Q 1/68
[52] U.S. Cl. .................. 536/23.1; 435/6; 435/91.2; 935/77; 935/78; 536/25.4
[58] Field of Search .................. 435/6, 91.2; 536/23.1, 536/25.4; 935/77, 78

[56] References Cited

U.S. PATENT DOCUMENTS 5,270,163  12/1993  Gold et al. .

FOREIGN PATENT DOCUMENTS

| 2 183 661 A | 6/1987 | United Kingdom . |
| WO 89/06694 | 7/1989 | WIPO . |
| WO 91/19813 | 12/1991 | WIPO . |
| 9203568 | 3/1992 | WIPO . |
| WO 92/14843 | 9/1992 | WIPO . |

OTHER PUBLICATIONS

Chang et al. (1990) Bio/Technology 8:122.
Davis et al. (1991) Bio/Technology 9:53.
Dombrowicz et al. (1993) Cell 75:969.
Haak-Frendscho et al. (1993) J. Immunology 151:351.
Haba and Nisonoff (1994) Proc. Natl. Acad. Sci. USA 91:604.
Peng et al. (1992) J. Immunology 148:129.
Pieken et al. (1991) Science 253:314.
Presta et al. (1993) J. Immunology 151:2623.
Saban et al. (1994) J. Allergy Clin. Immunol. 94:836.
Stampfli et al. (1994) Eur. J. Immunology 24:2161.
Sutton and Gould (1993) Nature 366:421.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman Proc. Natl. Acad Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Dombrowicz et al. (1993) Cell 75:969–976.
Pieken et al. (1991) Science 253:314–317.
Sutton and Gould (1993) Nature 366:421–428.
Nagpal et al., Autoimmunity 8(1):59–64 (1990).
Nagpal et al. (1990) 8:59 (Abstract).

*Primary Examiner*—Stephanie W. Zitomer
*Attorney, Agent, or Firm*—Swanson & Bratschun LLC

[57] ABSTRACT

This invention discloses high-affinity oligonucleotide ligands to human Immunoglobulin E (IgE), specifically RNA and ssDNA ligands having the ability to bind to IgE, and the methods for obtaining such ligands. The ligands are capable of inhibiting the interaction of IgE with its receptor.

7 Claims, No Drawings

HIGH-AFFINITY OLIGONUCLEOTIDE LIGANDS TO IMMUNOGLOBULIN E (IGE)

RELATED APPLICATIONS

This application is a Continuation-in-Part of U.S. patent application Ser. No. 07/714,131, filed Jun. 10, 1991, entitled Nucleic Acid Ligands now U.S. Pat. No. 5,475,096, which is a Continuation-in Part of U.S. patent application Ser. No. 07/536,428, filed Jun. 11, 1990, entitled Systematic Evolution of Ligands by Exponential Enrichment, now abandoned, U.S. patent application Ser. No. 07/964,624, filed Oct. 21, 1992, entitled Methods of Producing Nucleic Acid Ligands now U.S. Pat. No. 5,496,938, and U.S. patent application Ser. No. 08/317,403, filed Oct. 3, 1994, entitled High-Affinity Oligonucleotide Ligands to Immunoglobulin E (IgE).

FIELD OF THE INVENTION

Described herein are methods for identifying and preparing high-affinity nucleic acid ligands to Immunoglobulin E (IgE). The method utilized herein for identifying such nucleic acid ligands is called SELEX, an acronym for Systematic Evolution of Ligands by EXponential enrichment. Specifically disclosed herein are high-affinity nucleic acid ligands. The invention includes high-affinity RNA ligands which bind to IgE and inhibit its ability to interact with the IgE FcεRI receptor. The invention also includes single stranded DNA ligands which bind to IgE and inhibit its ability to interact with the IgE FcεRI receptor.

BACKGROUND OF THE INVENTION

Stimulation of mast cells and basophils upon contact of allergy-specific IgE antibodies with antigens, called immediate hypersensitivity, is one of the most powerful effector mechanisms of the mammalian immune system. Due to a combination of genetic predisposition and environmental stimuli, approximately 20% of the U.S. population is prone to develop an abnormally strong immediate hypersensitivity, a condition known as allergy. Physiological symptoms include increased vascular permeability, vasodilation, smooth muscle contraction, and local inflammation. These and other IgE dependent reactions can cause allergic diseases like allergic rhinitis (hay fever), asthma, atopic dermatitis (chronic skin irritations) and in the most severe cases can lead to anaphylactic shock, causing death of the individual by asphyxiation and cardiovascular collapse. Common environmental allergens are pollen, dust mites, certain foods, animal dander, fungal spores, and insect venoms.

The first exposure to a specific antigen can lead to the sensitization of the individual. The allergen binds with low specificity to pre-existing IgE in the plasma. This complex interacts with the low affinity receptor FcεRII on antigen presenting cells (APC). The antigen is internalized, proteolytically processed and transported to the surface of the APC by class II MHC molecules. Fragments of the antigen are thereby presented to CD4+ T helper cells which in turn activate IgE committed B cells to produce antigen-specific IgE. Normally IgE occurs in the human plasma at a concentration of about 0.2 μg/ml but in atopic patients this level can rise to a concentration of over 10 μg/ml.

Re-exposure to the allergen results in tight binding to the allergen-specific IgE present on the high-affinity receptor FcεRI on the surface of mast cells. Multivalent allergens cause the crosslinking of several receptors in the cell membrane. This triggers an intracellular signaling cascade, leading ultimately to the release of preformed mediators from cytoplasmic granules and the secretion of newly synthesized mediators. These mediators, notably histamines, leukotrienes, prostaglandins, and proteases, in turn cause the wide spectrum of symptoms of the allergic response. Furthermore, the release of chemotactic cytokines from the mast cell attracts and activates inflammatory cells to the location of antigen exposure. Finally, the release of IL-4 activates B cells to produce more antigen-specific IgE, thereby amplifying the allergic response. For a review, see Sutton Gould (1993) Nature 366:421–428.

Mounting evidence indicates that the IgE system has evolved to cope primarily with infections by parasitic worms like *Schistosoma mansoni*. In the absence of such parasites, IgE mediated responses seem to be dispensable and frequently lead to pathologic consequences. Supporting this hypothesis is the fact that murine strains deficient in IgE or the IgE high-affinity receptor (Dombrowicz et al. (1993) Cell 75:969–976) lack the anaphylactic response, but appear otherwise normal.

IgE is a 190 $K_D$ antibody consisting of two ε heavy chains (70 $K_D$) and two light chains (25 $K_D$). The heavy chains contain one variable domain ($V_H$) and four constant domains ($C_H1$ to $C_H4$). The light chains contain one variable domain ($V_L$) and one constant domain ($C_L$). Each of these immunoglobulin domains consists of about 100 residues and is stabilized by intramolecular sulfur bridges. The heavy and light chains are connected by intermolecular sulfur bridges.

The IgE molecule can be subdivided into the $F_{AB}$ (antigen binding) region, containing the variable and the first constant domains and the $F_c$ (crystalline) region, consisting of the remaining constant domains. The antigen binds to hypervariable sites within the variable region, whereas the IgE receptors bind to the $F_c$ region. The high-affinity IgE receptor FcεRI contacts a dodecapeptide sequence located at the N-terminus of the $C_H3$ domain and the low affinity IgE receptor FcεRII binds to the middle portion of the same domain (reviewed in Sutton Gould supra).

The IgE molecule is significantly bent, reducing its predicted length from 17.5 nm for a planar molecule to 7 nm. This bend occludes one of the two potential FcεRI receptor binding sites resulting in a monovalent IgE molecule which, in the absence of a multivalent allergen, cannot crosslink receptor molecules to initiate the allergic response.

To allow the antigen mediated triggering of the allergic response, IgE must form a complex with the high affinity receptor, FcεRI. FcεRI consists of four transmembrane polypeptides: α, β, and γ₂. The α subunit, FcεRI(α), contains two extracellular immunoglobulin domains and it is the second domain, α(2), that binds to the convex site of the IgE molecule. The dissociation constant of this interaction is approximately $10^{-10}$M (Sutton Gould, supra). The β and γ chains of FcεRI are necessary to anchor the receptor in the cell membrane, to allow receptor crosslinking, and for signal transduction to initiate the release of mediators from mast cells.

To inhibit immediate hypersensitivity numerous steps of the pathway can be targeted. It should be possible to prevent the synthesis of IgE by binding to and blocking the action of IL-4 or the IL-4 receptor, to prevent mast cell and basophil stimulation by blocking IgE or the FcεRI IgE receptor, to prevent release of mediators by blocking a step of the intracellular signaling pathway, or to prevent physiological responses of patients by blocking the released mediators. This work demonstrates the use of high-affinity oligonucleotides to human IgE to inhibit the interaction of IgE with the FcεRI receptor.

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment," now abandoned, U.S. patent application Ser. No. 07/714,131, filed Jun. 10, 1991, entitled "Nucleic Acid Ligands now U.S. Pat. No. 5,475,096," U.S. patent application Ser. No. 07/931,473, filed Aug. 17, 1992, entitled "Nucleic Acid Ligands," now U.S. Pat. No. 5,270,163 (see also WO91/19813), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands" describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," describes a SELEX-based method which achieves highly efficient partitioning between oligonucleotides having high and low affinity for a target molecule. U.S. patent application Ser. No. 07/964,624, filed Oct. 21, 1992, entitled "Methods of Producing Nucleic Acid Ligands" now U.S. Pat. No. 5,496,938 describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of known and novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" and U.S. patent application Ser. No. 08/234,997, filed Apr. 28, 1994, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

BRIEF SUMMARY OF THE INVENTION

The present invention includes methods of identifying and producing nucleic acid ligands to immunoglobulin E (IgE) and the nucleic acid ligands so identified and produced. Nucleic acid sequences are provided that are ligands to IgE. More particularly, RNA and ssDNA sequences are provided that are capable of binding specifically to IgE. The RNA sequences include 2'-$NH_2$ modified pyrimidines.

Also included in this invention are RNA and ssDNA ligands of IgE that are inhibitors of IgE receptor binding. Specifically, RNA and ssDNA ligands are identified and described which inhibit the interaction of IgE with the FcεRI IgE receptor and thereby inhibit the allergic response elicited by IgE.

Further included in this invention is a method of identifying nucleic acid ligands and nucleic acid ligand sequences to IgE comprising the steps of (a) preparing a candidate mixture of nucleic acids, (b) contacting the candidate mixture of nucleic acid ligands with IgE, (c) partitioning between members of said candidate mixture on the basis of affinity to IgE, and (d) amplifying the selected molecules to yield a mixture of nucleic acids enriched for nucleic acid sequences with a relatively higher affinity for binding to IgE.

More specifically, the present invention includes the RNA ligands to IgE identified according to the above-described method, including those ligands listed in Table 1 (SEQ ID NOS:7–41 and 43–48). Also included are RNA ligands to IgE that are substantially homologous to any of the given ligands and that have substantially the same ability to bind IgE and inhibit IgE receptor binding. Further included in this invention are RNA ligands to that have substantially the same structural form as the ligands presented herein and that have substantially the same ability to bind IgE and inhibit IgE receptor binding.

Additionally, the present invention includes the ssDNA ligands to IgE identified according to the above-described method, including those ligands listed in Tables 5 and 6 (SEQ ID NOS:51–111). Also included are ssDNA ligands to IgE that are substantially homologous to any of the given ligands and that have substantially the same ability to bind IgE and inhibit IgE receptor binding. Further included in this invention are ssDNA ligands to IgE that have substantially the same structural form as the ligands presented herein and that have substantially the same ability to bind IgE and inhibit IgE receptor binding.

The present invention also includes modified nucleotide sequences based on the RNA and ssDNA ligands identified herein and mixtures of the same.

DETAILED DESCRIPTION OF THE INVENTION

This application describes high-affinity nucleic acid ligands to IgE identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands now U.S. Pat. No. 5,496,938, U.S. patent application Ser. No. 07/931,473, filed Aug. 17, 1992, entitled Nucleic Acid Ligands, now U.S. patent No. 5,270,163, (see also WO 91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The methods described herein and the nucleic acid ligands identified by such methods are useful for both therapeutic and diagnostic purposes. Therapeutic uses include the treatment or prevention of diseases or medical conditions in human patients. Therapeutic uses may also include veterinary applications.

Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to IgE described herein may specifically be used for identification of the IgE protein.

SELEX provides high affinity ligands of a target molecule. This represents a singular achievement that is unprecedented in the field of nucleic acids research. The present invention applies the SELEX procedure to the specific target of IgE. In the Example section below, the experimental parameters used to isolate and identify the nucleic acid ligands to IgE are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 (now U.S. Pat. No. 5,496,938)methods are described for obtaining improved nucleic acid ligands after SELEX has been performed. The '938 patent, entitled Methods of Producing Nucleic Acid Ligands, is specifically incorporated herein by reference.

In the present invention, SELEX experiments were performed in order to identify RNA and ssDNA with specific high affinity for IgE from a degenerate library containing 40 or 60 random positions (40N or 60N). This invention includes the specific RNA ligands to IgE shown in Table 1 (SEQ ID NOS:7–41 and 43–48), identified by the methods described in Examples 1–3. This invention also includes the specific ssDNA ligands to IgE shown in Tables 5 and 6 (SEQ ID NOS:51–111), identified by the methods described in Examples 6, 7 and 10. The scope of the ligands covered by this invention extends to all nucleic acid ligands of IgE, modified and unmodified, identified according to the SELEX procedure. More specifically, this invention includes nucleic acid sequences that are substantially homologous to the ligands shown in Tables 1, 5 and 6. By substantially homologous it is meant a degree of primary sequence homology in excess of 70%, most preferably in excess of 80%. A review of the sequence homologies of the ligands of IgE shown in Tables 1, 5 and 6 show that sequences with little or no primary homology may have substantially the same ability to bind IgE. For these reasons, this invention also includes nucleic acid ligands that have substantially the same ability to bind IgE as the nucleic acid ligands shown in Tables 1, 5 and 6. Substantially the same ability to bind IgE means that the affinity is within a few orders of magnitude of the affinity of the ligands described herein. It is well within the skill of those of ordinary skill in the art to determine whether a given sequence—substantially homologous to those specifically described herein—has substantially the same ability to bind IgE.

This invention also includes the ligands as described above, wherein certain chemical modifications are made in order to increase the in vivo stability of the ligand or to enhance or mediate the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 9, 1993, entitled High Affinity Nucleic Acid Ligands Containing Modified Nucleotides which is specifically incorporated herein by reference. Other modifications are known to one of ordinary skill in the art. Such modifications may be made post-SELEX (modification of previously identified unmodified ligands) or by incorporation into the SELEX process.

The nucleic acid ligands to the IgE protein described herein are useful as pharmaceuticals and as diagnostic reagents.

The following Examples are provided to explain and illustrate the present invention and are not intended to be limiting of the invention.

Example 1 describes the various experimental procedures used in Examples 2–5. Example 2 describes a representative method for identifying RNA ligands by the SELEX method which bind IgE and determines the affinities the ligands have for IgE. Example 3 maps which regions of the ligands are necessary for IgE binding. Example 4 demonstrates the specificity of the ligands for Human IgE. Example 5 demonstrates that the ligands of the invention are capable of inhibiting the interaction between IgE and the FcεRI receptor. Example 6 describes the various experimental procedures used in Examples 7–10. Example 7 describes a representative method for identifying DNA ligands by the SELEX method which bind human IgE and presents the sequences and affinities the ligands have for IgE. Example 8 demonstrates the specificity of the ligands for Human IgE. Example 9 demonstrates that the DNA ligands are capable of inhibiting the interaction between IgE and the FcεRI receptor. Example 10 describes a representative method for identifying DNA ligands by the SELEX method which bind mouse IgE, presents the sequences, affinities, and specificity of the DNA ligands.

EXAMPLE 1

Experimental Procedures

The experimental procedures provided in this example will be used in subsequent examples and are provided here to streamline the description.

A. Materials.

Human IgE used in this SELEX procedure was purchased from Athens Research Technology (Athens, Ga.); Mouse was purchased from PharMingen (San Diego, Calif.). Biotinylated TAN IgE and the RBL cell lines, untransfected or transfected with the FcεRI receptor were a generous gift from Dr. Kinet (NIH) (Bethesda, Md.). 2' $NH_2$ modified CTP and UTP were prepared according to the method of Pieken et al. (1991) Science 253:314–317. DNA oligonucleotides were synthesized by Operon Technologies (Alameda, Calif.). All other reagents and chemicals were purchased from standard commercial sources.

B. SELEX.

The SELEX procedure has been described in detail in U.S. Pat. No. 5,270,163 (see also Tuerk and Gold (1990) Science 24:505–510). For the IgE experiments, the DNA templates were designed to contain 40 or 60 random nucleotides, flanked by 5' and 3' regions of fixed structure (shown in Table 2) designated 40N7 (SEQ ID NO:1) and 60N7 (SEQ ID NO:2), respectively. The fixed regions include DNA primer annealing sites for PCR and cDNA synthesis as well as the consensus T7 promoter region to allow in vitro transcription. Single-stranded DNA molecules were converted into double-stranded transcribable templates by PCR amplification. PCR conditions were 50 mM KCl, 10 mM Tris-Cl, pH 9, 0.1% Triton X-100, 3 mM $MgCl_2$, 0.5 mM of each dATP, dCTP, dGTP, and dTTP, and contained 0.1 units/μl of Taq DNA polymerase. Transcription reactions contained 5 μM DNA template, 5 units/μl T7 RNA polymerase, 40 mM Tris-Cl (pH 8.0), 12 mM $MgCl_2$, 5 mM DTT, 1 mM spermidine, 0.002% Triton X-100, 4% PEG 8000, 2 mM each of 2'-OH ATP, 2'-OH GTP, 2'-$NH_2$ CTP, 2'-$NH_2$ UTP, and 0.25 μM α-$^{32}$P 2'OH ATP. The RNA molecules were incubated with IgE protein in modified phosphate buffered saline (PBS), modified to contain 1 mM $Mg^{2+}$ ions, (138 mM NaCl, 2.7 mM KCl, 8.1 mM $Na_2HPO_4$, 1.1 mM $KH_2PO_4$, 1 mM $MgCl_2$, pH 7.4) for 10 min to allow binding to occur. IgE-RNA complexes were separated from unbound RNA by nitrocellulose filter partitioning. Bound RNA was isolated from filters by phenol/urea extraction. The RNA was reverse transcribed into cDNA by AMV reverse transcriptase (AMVRT) at 48° C. for 60 min in 50 mM Tris-Cl (pH 8.3), 60 mM NaCl, 6 mM Mg(OAc)$_2$, 10 mM DTT, 50 pmol DNA primer, 0.4 mM each of dNTPs, and 1 unit/μl AMVRT. PCR amplification of this cDNA resulted in approximately 500 pmol double-stranded DNA which was used to initiate the next round of SELEX.

C. Nitrocellulose Filter Partitioning.

For isolation of RNA molecules that bind tightly to IgE, the nitrocellulose filter partitioning method was used as described in the SELEX Patent Applications. Filter discs (nitrocellulose/cellulose acetate mixed matrix, 0.45 μm pore size, Millipore Corporation, Bedford, Mass.) were placed into a vacuum manifold and wetted with 5 ml of modified PBS buffer. $^{32}$P labeled RNA pools were incubated with serial dilutions of IgE in modified PBS for 10 min at 37° C. and aspirated through the filter discs which was followed immediately by a 5 ml modified PBS wash. The filter discs were air-dried and counted in a liquid scintillation counter (Beckmann Instruments, Palo Alto, Calif.).

To obtain equilibrium dissociation constants of RNA ligands to IgE the binding reaction:

$$R.P \rightarrow R+P$$

R=RNA
P=Protein
$K_D$=dissociation constant is converted to an equation for the fraction of RNA bound at equilibrium:

$$q = (f/2R_T)*(P_T+R_T+K_D-((P_T+R_T+K_D)^2-4P_TR_T)^{1/2})$$

q=fraction of RNA bound
$P_T$=total protein concentration
$R_T$=total RNA concentration
f=retention efficiency of RNA-protein complexes The average retention efficiency for RNA-IgE complexes on nitrocellulose filters is 0.8. $K_DS$ were determined by least square fitting of the data points using the KALEIDA-GRAPH™ graphic program (Synergy Software, Reading, Pa.).

D. Cloning and Sequencing.

During the last round of SELEX, PCR of cDNA was performed with the primers shown in Table 2 which contain recognition sites for the restriction endonucleases HindIII (5' primer 5P7H (SEQ ID NO:5)) and BamHI (3' primer 3P7B (SEQ ID NO:6)). Using these restriction sites the DNA sequences were inserted directionally into the vector. These plasmids were transformed into *E. coli* SURE™ strain (Stratagene, La. Jolla, Calif.). Plasmid DNA was prepared with the CLEARCUT™ miniprep kit (Stratagene, La Jolla, Calif.) and about 80 clones were sequenced with the SEQUENASE™ sequencing kit (United States Biochemical Corporation, Cleveland, Ohio).

E. Ligand Truncation.

Truncation experiments were carried out to determine the minimal sequence necessary for high affinity binding of the RNA ligands to IgE. For 3' boundary determination, RNA ligands were 5' end-labeled with $\gamma$-$^{32}$P-ATP using T4 polynucleotide kinase. 5' boundaries were established with 3' end-labeled ligands using $\alpha$-$^{32}$P-pCp and T4 RNA ligase. After partial alkaline hydrolysis, radiolabeled RNA ligands were incubated with IgE at concentrations ranging from 1 nM to 150 nM and protein-bound RNA was separated by nitrocellulose partitioning. RNA truncates were analyzed on a high-resolution denaturing polyacrylamide gel. A ladder of radioactively labeled ligands terminating with G-residues was generated by partial RNase T1 digestion and was used as markers.

F. IgE Receptor Binding Assay.

A cell-based enzyme linked immunosorbent assay (ELISA) was used to measure the ability of the high-affinity RNA ligands to inhibit binding of IgE to the FcεRI receptor. Rat basophilic leukemia (RBL) cell-line SX-38 which expresses the α, β and γ subunits of the human FcεRI IgE receptor was plated at a concentration of $10^5$ cells per well in 96 well flat-bottom microtiter plates. After overnight growth, the cells were washed three times in modified PBS and incubated for one hour at 37° C. in 30 μl of 1.5 μg/ml biotinylated TAN IgE. The cells were washed 3 more times and incubated in 30 μl of 1/100 dilution of horseradish peroxidase conjugated to avidin (Molecular Probes, Eugene, Oreg.) for one hour at 37° C. After three final washes, 30 μl of 3,3',5,5'-tetramethylbenzidine (TMB) substrate (Kirkegaard and Perry Laboratories, Gaithersburg, Md.) were added as a chromogenic substrate and the plate was immediately transferred to the microtiter plate reader (Bio-Tek Instruments, Winooski, Vt.) for analysis. The absorbance at 630 nM was measured every 60 sec over a time span of 15 min. The rate of color development is an indication of the extent of IgE binding to the FcεRI receptor and was determined from the linear part of absorbance versus time graphs (data not shown). To test the effectiveness of RNA ligands to inhibit IgE binding to the receptor, the biotinylated TAN IgE was pre-incubated with RNA at concentrations ranging from $10^{-5}$M to $3.3\times10^{-9}$M for 30 min at 37° C. As control reactions addition of RNA or IgE were omitted (maximum rate and background rate, respectively). The inhibition activities of the RNA ligands were determined using the following formula:

$$I_B = (R_R - B_R)/(M_R - B_R) * 100$$

$I_B$=relative percentage IgE bound
$R_R$=reaction rate
$B_R$=background rate
$M_R$=maximum rate Substituting transfected RBL SX-38 cells with the untransfected parental cell-line resulted in reaction rates similar to the background rate (data not shown). Values for the inhibition constant ($K_i$) were calculated based on the following estimates: $10^5$ cells per well and $10^5$ receptors per cell in 30 μl volume, resulting in a receptor concentration of $5\times10^{-10}$M. The IgE concentration in this assay was $8\times10^{-12}$M and the dissociation constant for the IgE/receptor complex is $10^{-10}$M.

EXAMPLE 2

RNA Ligands to IgE

A. SELEX.

In order to generate stable ligands to human IgE two SELEX experiments were performed with 2'-NH$_2$ pyrimidine modified RNA molecules using the methods described in Example 1. As shown in Table 2, these RNA pools differ in the number of random bases present in the central portion of the molecules: 40 nucleotides in the 40N7 (SEQ ID NO:1) SELEX and 60 nucleotides in the 60N7 (SEQ ID NO:2) SELEX experiment. The starting pools of $3\times10^{-14}$ RNA molecules (500 pmol) bind IgE with approximate affinities of greater than 50 μM. After 9 rounds of SELEX, the affinities of the evolving pools had improved about two orders of magnitude and did not shift further in subsequent rounds. Round 9 RNA was bulk sequenced and found to be non-random. Therefore, cDNA from this round was PCR amplified with primers containing restriction sites and cloned into pUC19. About 35 clones from each SELEX experiment were sequenced as shown in Table 1. The sequences were inspected by eye and analyzed using computer programs which perform alignments.

B. RNA Sequences.

25 out of 35 (40N7 SELEX) and 30 out of 34 (60N7 SELEX) sequenced clones were found to be unique. As shown in Table 1, these unique clones can be divided into four classes: high-affinity IgE ligand Groups A (SEQ ID NOS:7–18) and B (SEQ ID NOS:19–28), a group of unrelated high-affinity IgE ligands called orphan sequences (SEQ ID NOS:29–41) and nitrocellulose binding ligand Group C (not shown). It is interesting to note that all groups contain members of both 40N7 (SEQ ID NO:1) and 60N7 (SEQ ID NO:2) sequences. This indicates that independent SELEX experiments can result in the isolation of essentially identical ligands.

To crudely screen the ligands for their ability to bind to IgE, 2-point $K_D$S were determined for all clones (data not shown). Group C ligands containing the consensus motif: 5' G-G-G-(N$_{3-5}$)-G-U/C-G-G-A/U-G-G-G-G 3' (SEQ ID NO:42) were found to have high affinities for nitrocellulose instead of IgE and were not further analyzed.

Group A and group B ligands show characteristic conserved consensus domains of 10 and 20 nucleotides, respectively, immediately adjacent to the 5' fixed region as shown in Table 1. The conserved domains are:

| | |
|---|---|
| 5' GUG UGA AUG GUG UUG UGA GG 3' | (SEQ ID NO:43) |
| 5' GUG UGG GGC G 3' | (SEQ ID NO:44) |

The remaining bases of the variable regions 3' to these conserved stretches show no observable sequence conservation and are, therefore, unlikely to contribute to the specific binding of IgE.

C. Affinities.

The RNA ligands of group A, group B and most orphan sequences are high affinity IgE ligands and show very little binding to nitrocellulose. Dissociation constants for representative members of Group A and Group B as well as orphan sequences were determined by nitrocellulose filter binding experiments and the dissociation constants are listed in Table 3. Group A ligands show an average $K_D$ of approximately 150 nM, Group B ligands had an average $K_D$ of approximately 35 nM and orphan ligands had $K_D$s ranging from 50 nM to 250 nM.

EXAMPLE 3

Ligand Truncation

To determine the minimal sequence information necessary for high-affinity binding to IgE, truncation analysis was performed as described in Example 1 on representative members of Group A (IGEL1.1 (SEQ ID NO:7) and IGEL31.1 (SEQ ID NO:18), and Group B (IGEL2.1 (SEQ ID NO:20), and IGEL48.1 (SEQ ID NO:27). Table 1 shows that the 3' boundaries of the truncated ligands (SEQ ID NOS:45 and 46) are located, as expected, precisely at the end of the conserved consensus sequence motifs (SEQ ID NO:43) and (SEQ ID NO:44), in the variable region. This concurs with the hypothesis that these conserved sequence motifs are necessary for tight binding to IgE, whereas the degenerate remainder of the variable regions and the 3' fixed regions are dispensable. The 5' boundary determinations revealed that the entire 5' fixed regions, with the possible exception of the first three guanidine residues, are involved in binding to IgE. For technical purposes, further experiments were conducted with truncated ligands consisting of the intact 5' fixed region and the consensus domain, called IGEL1.2 (SEQ ID NO:47) (Group A truncate of IGEL1.1) and IGEL2.2 (SEQ ID NO:48) (Group B truncate of IGEL2.1). Since these truncates are not missing any 5' sequence information critical for transcription initiation, they transcribe efficiently and yield several hundred RNA molecules per DNA template in overnight in vitro transcription reactions (data not shown). Representative binding data for these truncated RNA ligands in direct comparison with their full-length counterparts are shown in Table 3. While the $K_D$ of IGEL2.2 is essentially unaffected by the truncation, IGEL1.2 actually binds several fold better as a truncate compared to the full-length IGEL1.1 ligand. This result demonstrates that the removal of nucleotides which are not contributing to the binding of a protein can increase the affinity of this interaction, possibly by allowing a tighter fit of the RNA to the surface of the protein.

EXAMPLE 4

Specificity of RNA Ligands to Human IgE

To test the specificity of the high-affinity interaction between the RNA ligands and human IgE, binding experiments were performed with different immunoglobulins as described in Example 1. Table 4 summarizes the results of these studies with rat, murine and a human-murine hybrid IgE. The $K_D$S for murine and rat IgE are estimated to be greater than 5 μM which is at least two orders of magnitude higher than the corresponding dissociation constants to human IgE. Furthermore, IgE ligands do not bind significantly to human IgG, a different immunoglobulin isotype (data not shown). These results indicate that the RNA ligands are very specific for human IgE and do not interact efficiently with related molecules.

In order to localize which part of the IgE molecule the RNA ligands are contacting, binding experiments were carried out with a hybrid IgE molecule. The light chains and the variable region of this TAN IgE are murine derived, whereas the constant portion of the heavy chains are human. As shown in Table 4, the affinities of ligands IGEL1.1 (SEQ ID NO:7) and IGEL1.2 (SEQ ID NO:47) are equivalent to those determined for the entirely human IgE. These results indicate that ligands IGEL1.1 and IGEL1.2 are contacting IgE at the $F_c$ portion. This part of the IgE molecule also harbors the contact region with the FcεRI receptor, making it potentially possible to competitively inhibit IgE binding to the receptor.

EXAMPLE 5

Inhibition of the IgE—FcεRI Inhibition

To directly test the ability of the RNA ligands to competitively inhibit the binding of IgE to the FcεRI receptor, a tissue culture cell based assay was performed as described in Example 1. Briefly, rat basophilic leukemia (RBL) cells that are expressing the human FcεRI receptor on the cell surface were incubated with biotinylated IgE. Using streptavidin conjugated horseradish peroxidase, the relative amount of IgE bound to the receptor can be determined by measuring the rate of-conversion of a chromogenic substrate. The rate in the absence of inhibiting RNA is defined as 100% activity and the rate in the absence of IgE is used to calculate the background which is subtracted from the conversion rates. The RNA species to be tested for competitive inhibition were pre-incubated with the IgE before the mixture was added to the RBL cells. Random RNA, the 40N7 (SEQ ID NO:1) and 60N7 (SEQ ID NO:2) starting pools and IGEL NC1, a scrambled version of ligand IGEL 1.2, do not show any significant inhibition of IgE binding to the FcεRI receptor (data not shown). However, Group A ligands IGEL1.1 (SEQ ID NO:7) and IGEL1.2 (SEQ ID NO:47) do inhibit this interaction as shown in Table 4. The inhibitory dissociation constants ($K_i$) determined in this assay, 44 nM for IGEL1.1 and 21 nM for IGEL1.2, correspond well with the previously calculated $K_D$ values of 77 nM and 36 nM, respectively, of these ligands for TAN IgE. These results show that binding of Group A ligands to IgE causes competitive inhibition of the interaction with the FcεRI receptor. The orphan ligands tested in this assay show varying degrees of inhibition and most of them appear to be weaker inhibitors than IGEL1.1 and IGEL1.2. Group B ligands IGEL2.1 (SEQ ID NO:20) and IGEL2.2 (SEQ ID NO:48) do not show significant inhibition (data not shown) although they bind IgE tightly. This observation indicates that Group A and Group B ligands either bind IgE at different areas or that the binding orients the Group B ligands differently as to not allow inhibition of the IgE/receptor interaction.

EXAMPLE 6

Experimental Procedures

A. Materials.

Materials used for Examples 6-10 are the same as those described in Example 1A.

B. SELEX.

The SELEX procedure has been described in detail in U.S. Pat. No. 5,270,163 (see also Tuerk and Gold (1990) Science 249; 505–510). The DNA template for the DNA SELEX experiments, 40NBHI, (Table 2; SEQ ID NO:112) was designed to contain 40 random nucleotides and is flanked by 5' and 3' regions of defined sequence used as primer annealing sites for PCR amplification (Table 2; SEQ ID NOS:49–50). Conditions for PCR amplifications were 2.5 µM 5' primer, 2.5 µM 3' primer, 50 mM KCl, 10 mM Tris-Cl, pH 9, 0.1% Triton X-100, 3 mM MgCl$_2$, 0.5 mM of each dATP, dCTP, dGTP, and dTTP, and contained 0.1 U/µl of Taq DNA polymerase.

Since the 3' primer contains two biotin molecules, the two DNA strands differ in molecular weight after amplification and were separated on denaturing polyacrylamide gels. To radioactively label the DNA molecules, 100–500 pmol of purified single stranded DNA were incubated in 50 mM Tris (pH 7.6), 10 mM MgCl$_2$, 5 mM dithiothreitol, 0.1 mM spermidine, 0.1 mM EDTA, 1.25 µM γ-$^{32}$P ATP with 0.2 U/µl T4 polynucleotide kinase at 37° C. for 1 hour.

The 5' labeled DNA molecules were incubated with in modified phosphate buffered saline (PBS), modified to contain 1 mM Mg$^{2+}$ ions, (138 mM NaCl, 2.7 mM KCl, 8.1 mM Na$_2$HPO$_4$, 1.1 mM KH$_2$PO$_4$, 1 mM MgCl$_2$, pH 7.4) for 10 min to allow binding to occur. Protein-DNA complexes were separated from unbound DNA by nitrocellulose filter partitioning and bound DNA was isolated from filters by phenol/urea extraction.

C. Nitrocellulose Filter Partitioning.

For isolation of DNA molecules that bind tightly to IgE the nitrocellulose filter partitioning method was used as described in the SELEX Patent Applications. Filter discs (nitrocellulose/cellulose acetate mixed matrix, 0.45 µm pore size, Millipore Corporation, Bedford, Mass.) were placed into a vacuum manifold and pre-Washed by aspiration of 5 ml of modified PBS buffer. $^{32}$P labeled DNA pools were incubated with serial dilutions of IgE in modified PBS for 10 min at 37° C. and aspirated through the filter discs which was followed immediately by a 5 ml modified PBS wash. The filter discs were air-dried and counted in a liquid scintillation counter (Beckmann Instruments, Palo Alto, Calif.).

To obtain equilibrium dissociation constants of DNA ligands to IgE the binding reaction:

$$D.P K_D \rightarrow D+P$$

D=DNA

P=Protein $K_D$=dissociation constant is converted to an equation for the fraction of DNA bound at equilibrium:

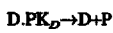

$$q(f/2D_T)*(P_T+D_T+K_D-((P_T+D_T+K_D)^2-4P_TD_T)^{1/2})$$

q=fraction of DNA bound $P_T$=total protein concentration $D_T$=total DNA concentration f=retention efficiency of DNA-protein complexes The average retention efficiency for DNA-IgE complexes on nitrocellulose filters is 0.5. $D_D$s were determined by least square fitting of the data points using the graphic program KALEIDAGRAPH™ Software Reading, Pa.).

D. Cloning and Sequencing.

During the last round of SELEX PCR amplification of the DNA pools was performed with primers which contain recognition sites for the restriction endonucleases HindIII (5' primer) (SEQ ID NO:5) and BamHI (3' primer) (SEQ ID NO: 6). Using these restriction sites, the DNA sequences were inserted directionally into the pUC9 vector. These recombinant plasmids were transformed into E. coli strain DH5a.

Plasmid DNA was prepared with the PERFECT prep kit (5'→3', Boulder, Colo.) and about 40 clones of each DNA SELEX experiment were sequenced with the Sequenase sequencing kit (United States Biochemical Corporation, Cleveland, Ohio).

F. IgE Receptor Binding Assay.

A cell-based enzyme linked immunosorbent assay (ELISA) was used to measure the ability of the high-affinity DNA ligands to inhibit binding of IgE to the FcεRI receptor. Rat basophilic leukemia (RBL) cell-line SX-38 which expresses the α, β and γ subunits of the human FcεRI receptor was plated at a concentration of $10^5$ cells per well in 96 well flat-bottom microtiter plates. After overnight growth, the cells were washed three times in modified PBS and incubated for one hour at 37° C. in 30 µl of 1.5 µg/ml biotinylated TAN IgE. The cells were washed 3 more times and incubated in 30 µl of 1/100 dilution of horseradish peroxidase (Molecular Probes, Eugene, Oreg.) conjugated to avidin for one hour at 37° C. After three final washes, 30 µl of 3,3',5,5'-tetramethylbenzidine (TMB) substrate, (Kirkegaard and Perry Laboratories, Gaithersburg, Md.) were added as a chromogenic substrate, and the plate was immediately transferred to the microtiter plate reader (Bio-Tek instruments, Winooski, Vt.) for analysis. The absorbance at 630 nM was measured every 60 seconds over a time span of 15 minutes. The rate of color development is an indication of the extent of IgE binding to the FcεRI receptor and was determined from the linear part of absorbance versus time graphs (data not shown). To test the effectiveness of DNA ligands to inhibit IgE binding to the receptor, the biotinylated TAN IgE was pre-incubated with DNA at concentrations ranging from $10^{-5}$M to $3.3\times10^{-9}$M for 30 min at 37° C. As control reactions, addition of DNA or IgE were omitted (maximum rate and background rate, respectively). The inhibition activities of the RNA ligands were determined using the following formula:

$$I_B=(R_R-B_R)/(M_R-B_R)\times100$$

$I_B$=relative percentage IgE bound
$R_R$=reaction rate
$B_R$=background rate
$M_R$=maximum rate Substituting transfected RBL SX-38 cells with the untransfected parental cell-line resulted in reaction rates similar to the background rate (data not shown). Values for the inhibition constant ($K_i$) were calculated based on the following estimates: $10^5$ cells per well and $10^5$ receptors per cell in 30 μl volume, resulting in a receptor concentration of $5\times10^{-10}$M. The IgE concentration in this assay was $8\times10^{-12}$M and the dissociation constant for the IgE/receptor complex is $10^{-10}$M.

EXAMPLE 7

DNA Ligands to Human IgE

A. SELEX.

In order to generate ligands to human IgE, a SELEX experiment was performed with DNA molecules using the methods described in Example 6. 2 nmole ($1.2\times10^{-15}$ molecules) of 40NBHI single stranded DNA were used to start SELEX against human IgE. The concentration of human IgE was $10^{-6}$M in the first round and was gradually reduced during subsequent rounds to $5\times10^{-10}$M in round 15. The DNA concentration was kept at a 10 fold excess in the first round and at a 2 fold excess in subsequent rounds. These conditions resulted in a retention of 0.1 to 6% of the total DNA on nitrocellulose filters. Binding of DNA to the filters in the absence of IgE was 10 to 400 fold lower. DNA molecules from round 15 were cloned into pUC9 and sequence information was obtained for 87 clones as shown in Table 5. The sequences were inspected by eye and aligned to reveal homologies.

B. Sequences.

42 out of 87 sequenced clones were found to be unique. As shown in Table 5 (SEQ ID NOS:51-92), these clones can be grouped into one family characterized by a conserved sequence motif which is 21 bases in length and is located in the 40 nucleotide random region. This motif can be folded into a stem—loop structure. Bases flanking the consensus sequence can base pair with each other, therefore extending the conserved stem by an additional 2 to 11 base pairs. Extensive covariation in this DNA ligand family indicates that no specific primary sequence is required in this stem extension. To determine the minimal sequence requirements for high affinity binding to human IgE, three single stranded DNA species were synthesized: D17.0 (SEQ ID NO:57), the full-length ligand of clone 17 (80 nucleotides); D17.1 (SEQ ID NO:93) containing the 21 base conserved motif with two times four flanking bases forming the stem extension (29 nucleotides); and 17.4 (SEQ ID NO:94) which extends D17.1 with four 5' G residues and four 3' C residues (37 nucleotides).

C. Affinities.

Affinities of representative DNA ligands for human IgE were determined by nitrocellulose filter binding experiments and the $K_D$s are listed in Table 7. During the 15 rounds of SELEX, the affinity of the DNA pool shifted more than three orders of magnitude from greater than 50 μM to 10 nM. Individual clones tested from this pool have affinities in the same range. The affinities were not expected to vary widely since the enriched DNA pool is very homogenous. Ligand D17.0 was picked for truncation experiments. Compared to the full-length ligand, the 29 base truncate D17.1, containing the conserved sequence motif and the 4 base pair extended stem, binds with a 8 fold weaker affinity to IgE. However, the affinity could be restored to the level of the full-length ligand by the addition of a 4 basepair stem resulting in the 37 base truncate D17.4. It is possible that the stem in D17.1 is not stable enough to prevent the formation of an alternative secondary structure and that the additional base pair in D17.4 lock in the conformation necessary for IgE binding.

EXAMPLE 8

Specificity of DNA Ligands to Human IgE

To test the specificity of the high-affinity interaction between the DNA ligands and human IgE, binding experiments were performed with different immunoglobulins. $K_D$s of ligand D17.4 for mouse IgE and human IgG were determined to be greater than 10 μM which is at least three orders of magnitude higher than the corresponding dissociation constants to human IgE. These result indicate that this DNA ligand is very specific for human IgE and does not bind efficiently to related molecules.

EXAMPLE 9

Inhibition of the IgE—FcεRI Interaction

To test the ability of the DNA ligands to competitively inhibit the binding of IgE to the FcεRI receptor, a tissue culture cell based assay was performed. Rat basophilic leukemia (RBL) cells that are expressing the human FcεRI receptor on the cell surface were incubated with biotinylated IgE. Using streptavidin conjugated horseradish peroxidase, the relative amount of IgE bound to the receptor was determined by measuring the rate of conversion of a chromogenic substrate. The rate in the absence of inhibiting DNA is defined as 100% activity and the rate in the absence of IgE is used to calculate the background which is subtracted from the conversion rates. The DNA species to be tested for competitive inhibition were pre-incubated with the IgE before the mixture was added to the RBL cells. Random DNA, the 40NBHI starting pool (SEQ ID NO:112) and D17NC, the randomized version of D17.4, do not show any significant inhibition of IgE binding to the FcεRI receptor. In contrast, DNA ligands D17.0 (SEQ ID NO:57) and D17.4 (SEQ ID NO:94) inhibit this interaction with estimated inhibitory dissociation constants ($K_i$) of approximately 40 nM. These values are in the same range as the previously calculated $K_D$ values of 10nM indicating that binding of D17.0 and D17.4 ligands to IgE causes competitive inhibition of the interaction with the FcεRI receptor.

EXAMPLE 10

DNA Ligands to Mouse IgE

A. SELEX.

In order to generate ligands to mouse IgE, a SELEX experiment was performed with DNA molecules using the methods described in Example 6. DNA ligands to mouse are useful for developing mouse models of allergic disease. 2 nmole ($1.2 \times 10^{-15}$ molecules) of 40NBHI single stranded DNA were used to start SELEX against mouse IgE. The concentration of mouse IgE was $10^{-6}$M in the first round and was graduately reduced during subsequent rounds to $5 \times 10^{-10}$M in round 15. The DNA concentration was kept at a 10 fold excess in the first round and at a 2 fold excess in subsequent rounds. These conditions resulted in a retention of 0.2 to 2.6% of the total DNA on nitrocellulose filters. Binding of DNA to the filters in the absence of IgE was 8 to 200 fold lower. DNA molecules from round 15 were cloned into pUC9 and sequence information was obtained for 24 clones as described in Example 6 A–D.

B. Sequences, Affinities, and Specificity of DNA ligands.

16 out of 24 sequenced clones were found to be unique (Table 6; SEQ ID NOS:95–111). Despite extensive inspection by eye and analysis with the help of alignment programs no obvious sequence families were identified. The ligands showing similarity are believed to be clonally derived PCR artifacts rather than independently isolated sequences. Furthermore, no similarities to the human IgE DNA ligands were identified. The affinities of the starting DNA pool and round 15 DNA pool for mouse IgE were determined by nitrocellulose filter binding experiments. During the SELEX experiment, the $K_D$ of the DNA pool shifted more than 50 fold from greater than 1 µM to 20 nM. The round 15 DNA pool enriched for mouse ligands was tested for binding to human IgE and the $K_D$ was found to be greater than 50 µM. Therefore, the mouse IgE ligands do not bind significantly better to human than random DNA.

TABLE 1

IgE Binding Ligands

| * | ** | SEQUENCE*** |
|---|---|---|
| | | Group A Sequences |
| 7 | 1.1 | GGGAGGACGAUGCGGUGCGGUGUGAAUGGUGUUGUGAGGUUACUGUACUUCCGGUGCGUGCAGACGACUCGCCCGA |
| 8 | 21.1 | GGGAGGACGAUGCGGUGCGGUGUGAACGGUGUUGUGAGGUUACUGUACUUCCGGUGCGUGCAGACGACUCGCCCGA |
| 9 | 22.1 | GGGAGGACGAUGCGGUGCGGUGCGAAUGGUGUUGUGAGGAGCCUAAAUACGCGAUUGGUCAGACGACUCGCCCGA |
| 10 | 23.1 | GGGAGGACGAUGCGGGUGUGAAUGGUGUUGUGAGGACGAGUCCCAGGGCCAGACGACUCGCCCGA |
| 11 | 24.1 | GGGAGGACGAUGCGGGUGUGAAUGGUGUUGUGAGGUGCGACGGCAUGCAGGAGGCCUGUGGUCAGACGACUCGCCCGA |
| 12 | 25.1 | GGGAGGACGAUGCGGGUGUGAAUGGUGUGAGGACUUAUCAGGGACUCCGUGGUCAGACGACUCGCCCGA |
| 13 | 26.1 | GGGAGGACGAUGCGGGUGUGAAUGGUGUGAGGUUACUGUGCACUUCGGCCUCAGACGACUCGCCCGA |
| 14 | 27.1 | GGGAGGACGAUGCGGGUGUGCAUGGUGUUGUGAGGCUGAGUAUAGGGCCUGCGUCAGACGACUCGCCCGA |
| 15 | 28.1 | GGGAGGACGAUGCGGGUGUGAAUGGUGUCGUGAGGAGGAUCGACAGCGAUCAGACGACUCGCCCGA |
| 16 | 29.1 | GGGAGGACGAUGCGGGUGUGAAUGGUGUCAAUGGUUCAAAUGGCCAUAUCGGCCAUAUUCUCGGCCAUGUGUGGCAUUGCGUUGCAUACAGACGACUCGCCCGA |
| 17 | 30.1 | GGGAGGACGAUGCGGGUGUGAAUGGUGUCGUGAGGAGUGAAAUAGGUUGAUAACCCCUUAACAACUGCGUGGGUCAGACGACUCGCCCGA |
| 18 | 31.1 | GGGAGGACGAUGCGGGUGUGAAUGGUGUGUGAGGUUCUCGACU TABLE 1-continued IgE Binding Ligands

| SEQ ID NO | IGEL numbers | SEQUENCE |
|---|---|---|
| 26 | 47.1 | GGGAGGACGAUGCGGGUGUGGGCGGAUAAUGAGUGAACAGAGUGAAAUUCCAGCGUACGCAGACUGUCGCAGACGCCCGA |
| 27 | 48.1 | GGGAGGACGAUGCGGGAGUGGGCGGAUGAGAGAGAUCAGAGAACUAGAAGUGAAUCUGAGCGUUGCGCAGACGACUCGCCCGA |
| 28 | 49.1 | GGGAGGACGAUGCGGGUGUGGGCGGAUAAUGAGUGAACAGAGUGAAAUUCCAGUAGCCAGAGACUGUGCGCAGACGACUCGCCCGA |
| 44 | Consensus | GUGUGGGGCG |
| 46 | Truncated | AGGACGAUGCGGGUGUGGGCG |
| 48 | 2.2 | GGGAGGACGAUGCGGGUGUGGGGCG |

Orphan Sequences

| | | |
|---|---|---|
| 29 | 3.1 | GGGAGGACGAUGCGGUCCAUCGAUUAGGGCGGUCGUGCUCGUGUAGUGUGUAGUGGCAGACGACUCGCCCGA |
| 30 | 4.1 | GGGAGGACGAUGCCGAUGCGCGACGGUAGUCUGGUAGGGCGUAGGCCUGUGACCGGAGAAUCCGACCAGACGACUCGCCCGA |
| 31 | 5.1 | GGGAGGACGAUGCCGAUGCGGUAUCGGUACGUGUUGGCUUGGGAAGGGUCCGACGGUCCAGACGACUCGCCCGA |
| 32 | 6.1 | GGGAGGACGAUGCCGAUGCGGUAGUCUGGUAGGGCGUAGGCCUGUGACCGGAGAAUCCGACCAGACGACUCGCCCGA |
| 33 | 7.1 | GGGAGGACGAUGCCGAUGCGGGAGACCGUGAACACAGUAUCACAGUUAAGGAUGCGCGCAGACGACUCGCCCGA |
| 34 | 8.1 | GGGAGGACGAUGCCGCCCGUCGAGGGCUAGGCGUAGAGAGUCUAACCGUGCCAGACGACUCGCCCGA |
| 35 | 9.1 | GGGAGGACGAUGCCGGGAACAGACGGGCCUCAGAGCGGGUUAGGGUUAGGGAUCGCGGACGACCGACUCGCCCGA |
| 36 | 10.1 | GGGAGGACGAUGCCGGGCCACCGCGGUCGGUUAGGGAUCGCGGACACCGACCACCUGACGGUCGACGUCGCCCGA |
| 37 | 11.1 | GGGAGGACGAUGCCGAUGCGGAACAGCACGAGUGUACCUAAGACACAGGCGAUGCACUCGUCGAAAUCAUAUAGUGACAGACGACUCGCCCGA |
| 38 | 13.1 | GGGAGGACGAUGCCGAUGCGGGGGCCGGGAAUCCAUGUGAGCGAACAGAGAGCCGUGUAUCCAUUCGUGUCAGACGACUCGCCCGA |
| 39 | 15.1 | GGGAGGACGAUGCCGAUGCCGAGCGGCGACGAGGUCGAACAGGGGUAGGGAAGAUCGUCUGAAGUAUGCGCCUUCCAGCCGUCAGACGACUCGCCCGA |
| 40 | 16.1 | GGGAGGACGAUGCCGGUGAGCCUUUAGGGGAAAUAGUGCAGAAUUGCUCAUGAAUCCGACUGUGUCGAGACCGACUCGCCCGA |
| 41 | 17.1 | GGGAGGACGAUGCCGGUGAGCCUUUAGGGGAGAUCGCACCUGAUCAAAGACGAUAGACGAGUCGCCCAGAGACGACUCGCCCGA |

*SEQ ID NO
**IGEL numbers
****nucleotide abbreviations C and U actually depict the modified nucleotides 2'-NH$_2$—C and 2'-NH$_2$—U

TABLE 2

| SEQ ID NO: | Nucleic Acid Sequence |
|---|---|
| | Starting RNAs For RNA SELEX Experiments: |
| | 40N7: |
| 1 | 5' GGGAGGACGAUGCGG [-40N-] CAGACGACUCGCCCGA 3' |
| | 60N7: |
| 2 | 5' GGGAGGACGAUGCGG [-60N-] CAGACGACUCGCCCGA 3' |
| | SELEX PCR Primers For RNA SELEX Experiments: |
| | 5P7: |
| 3 | 5' TAATACGACTCACTATAGGGAGGACGATGCGG 3' |
| | 3P7: |
| 4 | 5' TCGGGCGAGTCGTCTG 3' |
| | Cloning PCR Primers For RNA SELEX Experiments: |
| | 5P7H: |
| 5 | 5' CCGAAGCTTAATACGACTCACTATAGGGAGGACGATGCGG 3' |
| | 3P7B: |
| 6 | 5' GCCGGATCCTCGGGCGAGTCGTCTG 3' |
| 49 | 5' primer for DNA SELEX experiments: |
| | 5BH1: |
| | 5' CTACCTACGATCTGACTAGC 3' |
| 50 | 3' primer for DNA SELEX experiments: |
| | 3BBH1: |
| | 5' AJAJAGGAACTACATGAGAGTAAGC 3' |
| 112 | Starting DNA: |
| | 40NBH1 |
| | 5' CTACCTACGATCTGACTAGC [-40N-] GCTTACTCTCATGTAGTTCC 3' |

TABLE 3

| Group | SEQ ID NO: | Ligand | Dissociation Constant |
|---|---|---|---|
| A | 7 | IGEL1.1 | 138 nM |
| | 12 | IGEL25.1 | 186 nM |
| | 16 | IGEL29.1 | 141 nM |
| | 18 | IGEL31.1 | 134 nM |
| B | 20 | IGEL2.1 | 41 nM |
| | 23 | IGEL44.1 | 34 nM |
| | 27 | IGEL48.1 | 30 nM |
| | 28 | IGEL49.1 | 39 nM |
| Orphans | 29 | IGEL3.1 | 56 nM |
| | 30 | IGEL4.1 | 87 nM |
| | 31 | IGEL5.1 | 145 nM |
| | 33 | IGEL7.1 | 142 nM |
| | 34 | IGEL8.1 | 225 nM |
| | 35 | IGEL9.1 | 105 nM |
| | 36 | IGEL10.1 | 69 nM |
| | 37 | IGEL11.1 | 129 nM |
| | 38 | IGEL13.1 | 50 nM |
| Group A Truncate | 47 | IGEL1.2 | 19 nM |
| Group B Truncate | 48 | IGEL2.2 | 44 nM |

TABLE 4

| Protein | Ligand (SEQ ID NO:) | Dissociation Constant | Inhibition Constant |
|---|---|---|---|
| Murine IgE | IGEL1.2 (47) | ≧5 μM | |
| | IGEL2.2 (48) | ≧5 μM | |
| Rat IgE | IGEL1.2 (47) | ≧5 μM | |
| | IGEL2.2 (48) | ≧5 μM | |
| TAN IgE | IGEL1.1 (7) | 77 nM | 44 nM |
| | IGEL1.2 (47) | 36 nM | 21 nM |

TABLE 5

Human IgE

| SEQ ID NOS: | | |
|---|---|---|
| 51 | D151 | ctacctacgatctgactagc TACCCGCGATGAGAGTAAGTTTATCCGTGTACTCTTAGTG gcttactctcatgtagttcc |
| 52 | D161 | ctacctacgatctgactagc TACCCGCGTTGAGAGTAAGTTTATCCGTGTACTCTTAGTG gcttactctcatgtagttcc |
| 53 | D066 | ctacctacgatctgactagc ACAGCATGAGAGATATAGCTTTATCCGTGACTCTCAGTGG gcttactctcatgtagttcc |
| 54 | D160 | ctacctacgatctgactagc CAATTGCTGAAGGAAGCATTTATCCGTTCCTCTTAGTGGT gcttactctcatgtagttcc |
| 55 | D016 | ctacctacgatctgactagc CAACTGCTGAAGGAAGCATTTATCCGTTCCTCTTAGTGGT gcttactctcatgtagttcc |
| 56 | D054 | ctacctacgatctgactagc AGGTCATGCGAGTATGCTTTATCCGTAACCTCTCAGTGG gcttactctcatgtagttcc |
| 57 | D017 | ctacctacgatctgactagc CAATGAGTGTACCACGTTTATCCGTCCCTCCTAGTGGCGT gcttactctcatgtagttcc |
| 58 | D001 | ctacctacgatctgactagc CCCTGANGTGTNMAMKTTTGTWCCGTTYCTCCTAGTGGCGT gcttactctcatgtagttcc |
| 59 | D069 | ctacctacgatctgactagc GGCCGTAAGCAAACCTTTATCCGTAATCTCTCAGTGGGTA gcttactctcatgtagttcc |
| 60 | D165 | ctacctacgatctgactagc GTGMGCGGGATCTTTATYCGTTACTCTTAGTGGGTCTCG gcttactctcatgtagttcc |
| 61 | D051 | ctacctacgatctgactagc AAGGCGACTACTTTATCCGTTTCTCTTAGTGGGTATCCG gcttactctcatgtagttcc |
| 62 | D173 | ctacctacgatctgactagc AATGGTCCAGCTTTATCCGTCTCTTTCAGTGGGCGTCATT gcttactctcatgtagttcc |
| 63 | D012 | ctacctacgatctgactagc CTACHGCCCATTTATVCGTTCCTCCTAGTGGTGGGCTGCT gcttactctcatgtagttcc |

TABLE 5-continued

Human IgE

| SEQ ID NOS: | | | | |
|---|---|---|---|---|
| 64 | D019 | ctacctacgatctgactagc | RGCCGGGACATTTATCCGTTACTACTCAGTGGGTGAACTGTC | gcttactctcatgtagttcc |
| 65 | D029 | ctacctacgatctgactagc | WCCGGAGTACTTTATYCGTYCCTTCTAGTGGGTACCCGTA | gcttactctcatgtagttcc |
| 66 | D002 | ctacctacgatctgactagc | GGGCCGGAGCTTTATCCGTTACTCTCAGTGGGTGACTGTC | gcttactctcatgtagttcc |
| 67 | D067 | ctacctacgatctgactagc | GGGCCGGAGCTTTATTCCGTTACTCTCAGTGGGTGACTGTC | gcttactctcatgtagttcc |
| 68 | D023 | ctacctacgatctgactagc | CAAAGTTAATTTATNCGTCCCTCCTAGTGGTTAACAGCG | gcttactctcatgtagttcc |
| 69 | D153 | ctacctacgatctgactagc | CAAAGTTAATTTATCCGTCCCTCTCAGTGGTTAACAGCG | gcttactctcatgtagttcc |
| 70 | D170 | ctacctacgatctgactagc | CAAGGTTAATTTATYCGTCCCTCCCAGTGGTTAACAGCG | gcttactctcatgtagttcc |
| 71 | D059 | ctacctacgatctgactagc | GATGGGAGCTTTATCCGTTCACTCTCAGTGGGCTCCTCAG | gcttactctcatgtagttcc |
| 72 | D072 | ctacctacgatctgactagc | GATGGGAGCTTTATCCGTTCACTTTCAGTGGGCTCCTCAT | gcttactctcatgtagttcc |
| 73 | D053 | ctacctacgatctgactagc | CGAAGTTAATTTATSCGTCCCTCCTAGTGGYTTAACAGCG | gcttactctcatgtagttcc |
| 74 | D172 | ctacctacgatctgactagc | CTTGCTCCATTTATCCGTTTCTCCCAGTGGTGGTTGCATG | gcttactctcatgtagttcc |
| 75 | D061 | ctacctacgatctgactagc | CTACGCGCTTTATCCGTTTCTCCCAGTGGGCGGGCGTTC | gcttactctcatgtagttcc |
| 76 | D080 | ctacctacgatctgactagc | GTVSSGCTTTATCCGTTNCTCCCAGTGGGCGGGCRTTC | gcttactctcatgtagttcc |
| 77 | D169 | ctacctacgatctgactagc | GGCTTTATCCGTAACCTCTTAGTGGGCCGCNCGCTTCACA | gcttactctcatgtagttcc |
| 78 | D009 | ctacctacgatctgactagc | ATGGGAGAACACTTAGCCTTCATCCGTTCCTCCTAGTGGG | gcttactctcatgtagttcc |
| 79 | D052 | ctacctacgatctgactagc | CGCGCGTACGAGCACCTTCATCCGTCCCTCCTAGTGGGGT | gcttactctcatgtagttcc |
| 80 | D074 | ctacctacgatctgactagc | GGCCGTAASCAAGCCTTYWTCCGTMACCTACTYAGTGGGGKR | gcttactctcatgtagttcc |
| 81 | D159 | ctacctacgatctgactagc | NNNNNNNNCTCTTTCATCCGTACCTCCCAGTGGAGAACGC | gcttactctcatgtagttcc |
| 82 | D011 | ctacctacgatctgactagc | ACCGGAGTACTTCATCCGTCCCTTCTAGTGGGTACCCGTA | gcttactctcatgtagttcc |
| 83 | D073 | ctacctacgatctgactagc | TCCGGAGTACTTCATCCGTYCCTTCTAGTGGGTACCCGTA | gcttactctcatgtagttcc |
| 84 | D152 | ctacctacgatctgactagc | AGGGATGTTCATCCGTTCCTCTCAGTGGCATCCCGTGGCT | gcttactctcatgtagttcc |
| 85 | D156 | ctacctacgatctgactagc | NNNNGGTTCATCCGTTCCTTCTAGTGGCCACCTGGATGCA | gcttactctcatgtagttcc |
| 86 | D162 | ctacctacgatctgactagc | TGGCATTCATCCGTCTCTCCTAGTGGTGCCTTGTCCCCCA | gcttactctcatgtagttcc |
| 87 | D058 | ctacctacgatctgactagc | CCTTCATCCGTTACTCTTAGTGGGGGCTTGCGATTCGAGT | gcttactctcatgtagttcc |
| 88 | D056 | ctacctacgatctgactagc | TGCTGGACAATTGATCCGTTACTCTTAGTGGTTGTGTGCT | gcttactctcatgtagttcc |
| 89 | D021 | ctacctacgatctgactagc | ACGGGTGAGTTGATCCGTTACTCTTAGTGGTGAACCTTGT | gcttactctcatgtagttcc |
| 90 | D031 | ctacctacgatctgactagc | ACGGGTGAGTTGATCCGTCACTCTTAGTGGTGAACCTTGT | gcttactctcatgtagttcc |
| 91 | D068 | ctacctacgatctgactagc | ACAGGTGAGTTGATCCGTTACTCTTAGTGGTGAACCTTGT | gcttactctcatgtagttcc |
| 92 | D079 | ctacctacgatctgactagc | ACTGGTGAKTTGATCCGTCACTCTTAGTGGTGAWCCTTGT | gcttactctcatgtagttcc |
| 93 | D17.1 | | CACGTTTATCCGTCCCTCCTAGTGGCGTG | |
| 94 | D17.4 | | GGGGCACGTTTATCCGTCCCTCCTAGTGGCGTGCCCC | |

TABLE 6

Mouse IgE

| SEQ ID NO: | | | | |
|---|---|---|---|---|
| 95 | D114 | ctacctacgatctgactagc | GGCGTTTTACTTACTGGTCTTAGACCGGAGAGACACAGTC | gcttactctcatgtagttcc |
| 96 | D134 | ctacctacgatctgactagc | GGCGTTTTACGTGTACKGGTCATGTGAGRCSGGAGAGACACRGTK | gcttactctcatgtagttcc |
| 97 | D109 | ctacctacgatctgactagc | GATGGGNGGGGGACGTGCTGATTTCCCACTTCATATTTCGT | gcttactctcatgtagttcc |
| 98 | D119 | ctacctacgatctgactagc | GAGGGTGTGGGACGTGCTGATTTCCCACTTCATATTTCGT | gcttactctcatgtagttcc |
| 99 | D110 | ctacctacgatctgactagc | CTGGGKKTCCCGCGGAKCKGTTACCAGTTATGGGGCAAG | gcttactctcatgtagttcc |
| 100 | D129 | ctacctacgatctgactagc | CTGGGGGTSCCGCGGAGCGTGTTACCAGTTATGGGGCAAT | gcttactctcatgtagttcc |
| 101 | D131 | ctacctacgatctgactagc | CTGGGGGTCCCGCGTAGCGTGTTACCAGTTATGGGGCAAT | gcttactctcatgtagttcc |
| 102 | D128 | ctacctacgatctgactagc | CCTACCGTCGKCGCGGTTAAGGAAACTACBGCCTTTTACB | gcttactctcatgtagttcc |
| 103 | D101 | ctacctacgatctgactagc | ACCGCTAGTTTCGAGGTTGGACGTGTTTGCCGTGTCGATT | gcttactctcatgtagttcc |
| 104 | D101 | ctacctacgatctgactagc | ACCGCTAGTTTCGAGGTTGGACGTGTTTGCCGTGTCGATT | gcttactctcatgtagttcc |
| 105 | D102 | ctacctacgatctgactagc | GTTGGACGGTTACGTTTCCTCATGGCAACCCAGCTAGATC | gcttactctcatgtagttcc |
| 106 | D112 | ctacctacgatctgactagc | TTTCCCTCGACGGGTGCCCACTGCGGCATGGGTTAAGA | gcttactctcatgtagttcc |
| 107 | D113 | ctacctacgatctgactagc | TGGGGCAGCTTTGCGNGGGTCCTACGTTTTACDTTTGCC | gcttactctcatgtagttcc |
| 108 | D121 | ctacctacgatctgactagc | NNCGTCCTTCCAGTGGTGGAGTACCACCCGTCCGCACTT | gcttactctcatgtagttcc |
| 109 | D124 | ctacctacgatctgactagc | CGCGGGTGATCGGATTRCCCTGCATCTCCRCCTGATTCTT | gcttactctcatgtagttcc |
| 110 | D127 | ctacctacgatctgactagc | GATNGCGTTTCGATACTGCTTCTGCGGAGTCACACAGCTC | gcttactctcatgtagttcc |
| 111 | D135 | ctacctacgatctgactagc | AGGCGGGTNCCCTCTGGCGGAACACTTTGCTGTTGTCCT | gcttactctcatgtagttcc |

TABLE 7

| Ligand | $K_D$ |
|---|---|
| 40 NBHI | ≥50 μM |
| Round 15 human IgE Ligand enriched pool | 10 nM |
| D2.0 | 6 nM |
| D11.0 | 8 nM |
| D31.0 | 22 nM |
| D17.0 | 9 nM |
| D17.1 | 82 nM |

TABLE 7-continued

| Ligand | K_D |
|---|---|
| D17.4 | 10 nM |
| D17NC | ≧50 μM |

We claim:

1. A nucleic acid ligand to the $F_c$ portion of IgE identified according to the method comprising:
   a) preparing a candidate mixture of nucleic acids;
   b) contacting said candidate mixture of nucleic acids with IgE, wherein nucleic acids having an increased affinity to IgE relative to the candidate mixture may be partitioned from the remainder of the candidate mixture;
   c) partitioning the increased affinity nucleic acids from the remainder of the candidate mixture; and
   d) amplifying the increased affinity nucleic acids to yield a mixture of nucleic acids enriched for nucleic acids with relatively higher affinity and specificity for binding to IgE, whereby a nucleic acid ligand to IgE may be identified.

2. The nucleic acid ligand of claim 1 wherein said nucleic acid ligand comprises 2'-amino (2'-NH$_2$) modified ribonucleic acids.

3. A purified and isolated non-naturally occurring RNA ligand to IgE wherein said ligand is selected from the group consisting of the sequences set forth in Table 1.

4. A purified and isolated non-naturally occurring RNA ligand to IgE comprising the sequences selected from the group consisting of SEQ ID NOS: 45 and 46.

5. The ligand of claim 4 comprising the sequence of SEQ ID NO:45.

6. A purified and isolated non-naturally occurring DNA ligand to IgE wherein said ligand is selected from the group consisting of the sequences set forth in Tables 5 and 6.

7. A purified and isolated non-naturally occurring nucleic acid ligand to the $F_c$ portion of IgE.

* * * * *

SEQUENCE LISTING ( 1 ) GENERAL INFORMATION:

( i i i ) NUMBER OF SEQUENCES: 112

( 2 ) INFORMATION FOR SEQ ID NO:1:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:1:

```
GGGAGGACGA UGCGGNNNNN NNNNNNNNNN NNNNNNNNNN NNNNNNNNNN        50
NNNNNCAGAC GACUCGCCCG A                                       71
```

( 2 ) INFORMATION FOR SEQ ID NO:2:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:2:

```
GGGAGGACGA UGCGGNNNNN NNNNNNNNNN NNNNNNNNNN NNNNNNNNNN        50
NNNNNNNNNN NNNNNNNNNN NNNNNCAGAC GACUCGCCCG A                 91
```

( 2 ) INFORMATION FOR SEQ ID NO:3:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:3:

```
TAATACGACT CACTATAGGG AGGACGATGC GG                           32
```

( 2 ) INFORMATION FOR SEQ ID NO:4:

( i ) SEQUENCE CHARACTERISTICS:
    ( A ) LENGTH: 16
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:4:

TCGGGCGAGT CGTCTG                            16

( 2 ) INFORMATION FOR SEQ ID NO:5:

( i ) SEQUENCE CHARACTERISTICS:
    ( A ) LENGTH: 40
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:5:

CCGAAGCTTA ATACGACTCA CTATAGGGAG GACGATGCGG          40

( 2 ) INFORMATION FOR SEQ ID NO:6:

( i ) SEQUENCE CHARACTERISTICS:
    ( A ) LENGTH: 25
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:6:

GCCGGATCCT CGGGCGAGTC GTCTG                   25

( 2 ) INFORMATION FOR SEQ ID NO:7:

( i ) SEQUENCE CHARACTERISTICS:
    ( A ) LENGTH: 71
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:7:

GGGAGGACGA UGCGGGUGUG AAUGGUGUUG UGAGGUUACU GUACUUCGGU   50

GGCUGCAGAC GACUCGCCCG A                    71

( 2 ) INFORMATION FOR SEQ ID NO:8:

( i ) SEQUENCE CHARACTERISTICS:
    ( A ) LENGTH: 71
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:8:

GGGAGGACGA UGCGGGUGUG AACGGUGUUG UGAGGUUACU GUACUUCGGU      50

GGCUGCAGAC GACUCGCCCG A      71

( 2 ) INFORMATION FOR SEQ ID NO:9:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:9:

GGGAGGACGA UGCGGGUGCG AAUGGUGUUG UGAGGAGCCU AAAUACGCGA      50

UUGGUCAGAC GACUCGCCCG A      71

( 2 ) INFORMATION FOR SEQ ID NO:10:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:10:

GGGAGGACGA UGCGGGUGUG AAUGGUGUUG UGAGGACUCG GAAGUUCCCC      50

AGGGCCAGAC GACUCGCCCG A      71

( 2 ) INFORMATION FOR SEQ ID NO:11:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:11:

GGGAGGACGA UGCGGGUGUG AAUGGUGUUG CGAGGCAUGC AGGAGGCGCU      50

GUGGUCAGAC GACUCGCCCG A      71

( 2 ) INFORMATION FOR SEQ ID NO:12:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:12:

```
GGGAGGACGA  UGCGGGUGUG  AAUGGUGUCG  UGAGGACUUA  UCAGGCUCCG    50
UGGUGCAGAC  GACUCGCCCG  A                                     71
```

( 2 ) INFORMATION FOR SEQ ID NO:13:

( i ) SEQUENCE CHARACTERISTICS:
        ( A ) LENGTH: 69
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:13:

```
GGGAGGACGA  UGCGGGUGUG  AAUGGUGUUG  UGAGGUUACU  GCACUUCGGC    50
GCUCAGACGA  CUCGCCCGA                                         69
```

( 2 ) INFORMATION FOR SEQ ID NO:14:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:14:

```
GGGAGGACGA  UGCGGGUGUG  CAUGGUGUUG  UGAGGCUGAG  UAUAGGGGCC    50
UGCGUCAGAC  GACUCGCCCG  A                                     71
```

( 2 ) INFORMATION FOR SEQ ID NO:15:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:15:

GGGAGGACGA UGCGGGUGUG AAUGGUGUCG UGAGGAUGGA UUCGACAUGA    50

GCGAUCAGAC GACUCGCCCG A    71

( 2 ) INFORMATION FOR SEQ ID NO:16:

( i ) SEQUENCE CHARACTERISTICS:
        ( A ) LENGTH: 94
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:16:

GGGAGGACGA UGCGGGUGUC AAUGGUGUUG CGAGGCAAAA AUAACCAGCG    50

CAUAUUCUCG GCCAUGUUGG CGUGCAUACA GACGACUCGC CCGA    94

( 2 ) INFORMATION FOR SEQ ID NO:17:

( i ) SEQUENCE CHARACTERISTICS:
        ( A ) LENGTH: 90
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:17:

GGGAGGACGA UGCGGGUGCG AAUGGUGUUG UGAGGAGUGA AUAUAGGUGG    50

AUACCCCUUA ACAACUGCGU GGGUCAGACG ACUCGCCCGA    90

( 2 ) INFORMATION FOR SEQ ID NO:18:

( i ) SEQUENCE CHARACTERISTICS:
        ( A ) LENGTH: 90
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:18:

GGGAGGACGA UGCGGGUGUG AAUGGUGUUG UGAGGUUCUC GACUGUUUGU    50

GUCUAGCCGU ACUUUAGCCU CGGCCAGACG ACUCGCCCGA    90

( 2 ) INFORMATION FOR SEQ ID NO:19:

( i ) SEQUENCE CHARACTERISTICS:

( A ) LENGTH: 71
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All C's are 2'-NH2 cytosine ( i x ) FEATURE:
( D ) OTHER INFORMATION: All U's are 2'-NH2 uracil ( x i ) SEQUENCE DESCRIPTION: SEQ ID NO:19:

GGGAGGACGA UGCGGGUGAG GGGCGAAUGG AGAACAUGAG ACAAGGAGAA  50

UGCGGCAGAC GACUCGCCCG A  71

( 2 ) INFORMATION FOR SEQ ID NO:20:

( i ) SEQUENCE CHARACTERISTICS:
( A ) LENGTH: 71
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All C's are 2'-NH2 cytosine ( i x ) FEATURE:
( D ) OTHER INFORMATION: All U's are 2'-NH2 uracil ( x i ) SEQUENCE DESCRIPTION: SEQ ID NO:20:

GGGAGGACGA UGCGGGUGUG GGGCGAAUGA GAAACGUUAC CAGGAAAUGC  50

GACUGCAGAC GACUCGCCCG A  71

( 2 ) INFORMATION FOR SEQ ID NO:21:

( i ) SEQUENCE CHARACTERISTICS:
( A ) LENGTH: 71
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All C's are 2'-NH2 cytosine ( i x ) FEATURE:
( D ) OTHER INFORMATION: All U's are 2'-NH2 uracil ( x i ) SEQUENCE DESCRIPTION: SEQ ID NO:21:

GGGAGGACGA UGCGGGAGUG GGGCGAAGGU AAUGUUGAGA CGAUGUAAGA  50

CUGGUCAGAC GACUCGCCCG A  71

( 2 ) INFORMATION FOR SEQ ID NO:22:

( i ) SEQUENCE CHARACTERISTICS:
( A ) LENGTH: 71
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All C's are 2'-NH2 cytosine ( i x ) FEATURE:

( D ) OTHER INFORMATION: All U's are 2'-NH2 uracil ( x i ) SEQUENCE DESCRIPTION: SEQ ID NO:22:

GGGAGGACGA UGCGGGCGUG GGGCGAUUCA UAUCAACUGC UUAAGGUCAC    50

GGGUCCAGAC GACUCGCCCG A    71

( 2 ) INFORMATION FOR SEQ ID NO:23:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:23:

GGGAGGACGA UGCGGGUGCG GGGCGAGUAU AUGAAACUUG GCUUGGUAAU    50

GAUCAGAAGU AGUGAGAACU GGGUGCAGAC GACUCGCCCG A    91

( 2 ) INFORMATION FOR SEQ ID NO:24:

( i ) SEQUENCE CHARACTERISTICS:
        ( A ) LENGTH: 90
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:24:

GGGAGGACGA UGCGGGAGUG GGGCGUAGGA UUUGCCACUU GGAUUUGGAC    50

AGUGAGCAUC AGAGUCAUCA CCGCCAGACG ACUCGCCCGA    90

( 2 ) INFORMATION FOR SEQ ID NO:25:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:25:

GGGAGGACGA UGCGGGAGUG GGGCGGAAUA ACUAUGUGUG CGUAAUUGUC    50

CUGUCGCGGU GUCACGAACC UUGUGCAGAC GACUCGCCCG A    91

( 2 ) INFORMATION FOR SEQ ID NO:26:

( i ) SEQUENCE CHARACTERISTICS:
    ( A ) LENGTH: 91
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:26:

```
GGGAGGACGA UGCGGGUGUG GGGCGGAUAA UGAGUGAACA GAGUGAAAUU      50
CCAGCGUACG CAGACUGUGC UGUCGCAGAC GACUCGCCCG A               91
```

( 2 ) INFORMATION FOR SEQ ID NO:27:

( i ) SEQUENCE CHARACTERISTICS:
    ( A ) LENGTH: 91
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:27:

```
GGGAGGACGA UGCGGGAGUG GGGCGAUGAG AGAGAUCAGA GAACUAGAAG      50
UGAUACAAAA UCUGAGGUUG UUGCGCAGAC GACUCGCCCG A               91
```

( 2 ) INFORMATION FOR SEQ ID NO:28:

( i ) SEQUENCE CHARACTERISTICS:
    ( A ) LENGTH: 91
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:28:

```
GGGAGGACGA UGCGGGUGUG GGGCGGAUAA UGAGUGAACA GAGUGAAAUU      50
CCAGUGUAGC CAGACUGUGC UGUCGCAGAC GACUCGCCCG A               91
```

( 2 ) INFORMATION FOR SEQ ID NO:29:

( i ) SEQUENCE CHARACTERISTICS:
    ( A ) LENGTH: 71
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
  ( D ) OTHER INFORMATION: All U's are 2'-NH2 uracil ( x i ) SEQUENCE DESCRIPTION: SEQ ID NO:29:

GGGAGGACGA UGCGGUCCAU CGAUUAGGCG GUCGUGCUGG UGUAGUGUGU    50

AGUGGCAGAC GACUCGCCCG A    71

( 2 ) INFORMATION FOR SEQ ID NO:30:

( i ) SEQUENCE CHARACTERISTICS:
    ( A ) LENGTH: 71
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:30:

GGGAGGACGA UGCGGACGGU AGUCUGGUAG GCGCUGUGAC GGCGAGAAUC    50

CGGACCAGAC GACUCGCCCG A    71

( 2 ) INFORMATION FOR SEQ ID NO:31:

( i ) SEQUENCE CHARACTERISTICS:
    ( A ) LENGTH: 70
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:31:

GGGAGGACGA UGCGGGUAUC GGUACGUGUU GGCUUGGGAA GGGGUCCGAC    50

GGUGCAGACG ACUCGCCCGA    70

( 2 ) INFORMATION FOR SEQ ID NO:32:

( i ) SEQUENCE CHARACTERISTICS:
    ( A ) LENGTH: 71
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:32:

GGGAGGACGA UGCGGACGGU AGUCUGGUAG GCGCUGUGAC GCCGAGAAUC    50

CGGAUCAGAC GACUCGCCCG A    71

( 2 ) INFORMATION FOR SEQ ID NO:33:

( i ) SEQUENCE CHARACTERISTICS:
  ( A ) LENGTH: 69
  ( B ) TYPE: nucleic acid
  ( C ) STRANDEDNESS: single
  ( D ) TOPOLOGY: linear ( i i ) MOLECULE TYPE: RNA ( i x ) FEATURE:
  ( D ) OTHER INFORMATION: All C's are 2'-NH2 cytosine ( i x ) FEATURE:
  ( D ) OTHER INFORMATION: All U's are 2'-NH2 uracil ( x i ) SEQUENCE DESCRIPTION: SEQ ID NO:33:

| | | | | | |
|---|---|---|---|---|---|
| GGGAGGACGA | UGCGGAGACG | CGUGAACACU | AGUAUCACAG | UUAAGGAUGC | 50 |
| GCGCAGACGA | CUCGCCCGA | | | | 69 |

( 2 ) INFORMATION FOR SEQ ID NO:34:

( i ) SEQUENCE CHARACTERISTICS:
  ( A ) LENGTH: 70
  ( B ) TYPE: nucleic acid
  ( C ) STRANDEDNESS: single
  ( D ) TOPOLOGY: linear ( i i ) MOLECULE TYPE: RNA ( i x ) FEATURE:
  ( D ) OTHER INFORMATION: All C's are 2'-NH2 cytosine ( i x ) FEATURE:
  ( D ) OTHER INFORMATION: All U's are 2'-NH2 uracil ( x i ) SEQUENCE DESCRIPTION: SEQ ID NO:34:

| | | | | | |
|---|---|---|---|---|---|
| GGGAGGACGA | UGCGGACCGC | CCGUCGAGGG | CUAGGCGUAG | AGUCUAACCG | 50 |
| GUGCCAGACG | ACUCGCCCGA | | | | 70 |

( 2 ) INFORMATION FOR SEQ ID NO:35:

( i ) SEQUENCE CHARACTERISTICS:
  ( A ) LENGTH: 91
  ( B ) TYPE: nucleic acid
  ( C ) STRANDEDNESS: single
  ( D ) TOPOLOGY: linear ( i i ) MOLECULE TYPE: RNA ( i x ) FEATURE:
  ( D ) OTHER INFORMATION: All C's are 2'-NH2 cytosine ( i x ) FEATURE:
  ( D ) OTHER INFORMATION: All U's are 2'-NH2 uracil ( x i ) SEQUENCE DESCRIPTION: SEQ ID NO:35:

| | | | | | |
|---|---|---|---|---|---|
| GGGAGGACGA | UGCGGGCGGG | GAACAGACGG | CUCAGAGCGG | CACGAUUGUC | 50 |
| AGCCAGCAAU | UAUAUCGUGU | UGAUGCAGAC | GACUCGCCCG | A | 91 |

( 2 ) INFORMATION FOR SEQ ID NO:36:

( i ) SEQUENCE CHARACTERISTICS:
  ( A ) LENGTH: 91
  ( B ) TYPE: nucleic acid
  ( C ) STRANDEDNESS: single
  ( D ) TOPOLOGY: linear ( i i ) MOLECULE TYPE: RNA ( i x ) FEATURE:
  ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:36:

GGGAGGACGA UGCGGGCCAC GCGUGGUUAG GGAUCGCGGA CAGCACAAAU        50

CGAAUUUGAU UCGCACCUGG ACGGUCAGAC GACUCGCCCG A                 91

( 2 ) INFORMATION FOR SEQ ID NO:37:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:37:

GGGAGGACGA UGCGGAACAG CACGAGUGUA CCUAAGACAG GCGAUGGCAC        50

UCGUGGUCGA AAUCAUAUAG UGAUGCAGAC GACUCGCCCG A                 91

( 2 ) INFORMATION FOR SEQ ID NO:38:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:38:

GGGAGGACGA UGCGGGACGG GGGCGGAAUC AUGCAUGUGA GCGAACAGAG        50

AGAGAGCCGU GUAUCCAUUC GUGGUCAGAC GACUCGCCCG A                 91

( 2 ) INFORMATION FOR SEQ ID NO:39:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:39:

GGGAGGACGA UGCGGAGGCG ACGAGGUGGA CAGGGGUAGG GAAGAUCGUC        50

UGAAGUAUGC GUCCUUCCAG CCCGUCAGAC GACUCGCCCG A                 91

( 2 ) INFORMATION FOR SEQ ID NO:40:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:40:

```
GGGAGGACGA UGCGGUGGAG CCUUUAGGGG GAAUAGUUGG CAGAAUUGCA        50
GCUCAUGUAA UCUCGACUGU GUGUGCAGAC GACUCGCCCG A                 91
```

( 2 ) INFORMATION FOR SEQ ID NO:41:

( i ) SEQUENCE CHARACTERISTICS:
        ( A ) LENGTH: 90
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:41:

```
GGGAGGACGA UGCGGUGGAG CCUUUAGGGG GAUCGCACCU GAUCAAAGAC        50
GCAGUAUCGA UAGACUUGCG UGCCCAGACG ACUCGCCCGA                   90
```

( 2 ) INFORMATION FOR SEQ ID NO:42:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( i x ) FEATURE:
        ( D ) OTHER INFORMATION: N at position 4 is 3-5
                nucleotides ( i x ) FEATURE:
        ( D ) OTHER INFORMATION: N at position 6 is U or C ( i x ) FEATURE:
        ( D ) OTHER INFORMATION: N at position 9 is A or U ( x i ) SEQUENCE DESCRIPTION: SEQ ID NO:42:

```
GGGNGNGGNG GGG
```

( 2 ) INFORMATION FOR SEQ ID NO:43:

( i ) SEQUENCE CHARACTERISTICS:

(A) LENGTH: 20
(B) TYPE: nucleic acid
(C) STRANDEDNESS: single
(D) TOPOLOGY: linear (ii) MOLECULE TYPE: RNA (ix) FEATURE:
    (D) OTHER INFORMATION: All C's are 2'-NH2 cytosine (ix) FEATURE:
    (D) OTHER INFORMATION: All U's are 2'-NH2 uracil (xi) SEQUENCE DESCRIPTION: SEQ ID NO:43:

GUGUGAAUGG UGUUGUGAGG  20

(2) INFORMATION FOR SEQ ID NO:44:

(i) SEQUENCE CHARACTERISTICS:
    (A) LENGTH: 10
    (B) TYPE: nucleic acid
    (C) STRANDEDNESS: single
    (D) TOPOLOGY: linear (ii) MOLECULE TYPE: RNA (ix) FEATURE:
    (D) OTHER INFORMATION: All C's are 2'-NH2 cytosine (ix) FEATURE:
    (D) OTHER INFORMATION: All U's are 2'-NH2 uracil (xi) SEQUENCE DESCRIPTION: SEQ ID NO:44:

GUGUGGGGCG  10

(2) INFORMATION FOR SEQ ID NO:45:

(i) SEQUENCE CHARACTERISTICS:
    (A) LENGTH: 32
    (B) TYPE: nucleic acid
    (C) STRANDEDNESS: single
    (D) TOPOLOGY: linear (ii) MOLECULE TYPE: RNA (ix) FEATURE:
    (D) OTHER INFORMATION: All C's are 2'-NH2 cytosine (ix) FEATURE:
    (D) OTHER INFORMATION: All U's are 2'-NH2 uracil (xi) SEQUENCE DESCRIPTION: SEQ ID NO:45:

AGGACGAUGC GGGUGUGAAU GGUGUUGUGA GG  32

(2) INFORMATION FOR SEQ ID NO:46:

(i) SEQUENCE CHARACTERISTICS:
    (A) LENGTH: 22
    (B) TYPE: nucleic acid
    (C) STRANDEDNESS: single
    (D) TOPOLOGY: linear (ii) MOLECULE TYPE: RNA (ix) FEATURE:
    (D) OTHER INFORMATION: All C's are 2'-NH2 cytosine (ix) FEATURE:
    (D) OTHER INFORMATION: All U's are 2'-NH2 uracil (xi) SEQUENCE DESCRIPTION: SEQ ID NO:46:

AGGACGAUGC GGGUGUGGGG CG  22

( 2 ) INFORMATION FOR SEQ ID NO:47:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:47:

GGGAGGACGA UGCGGGUGUG AAUGGUGUUG UGAGG           35

( 2 ) INFORMATION FOR SEQ ID NO:48:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:48:

GGGAGGACGA UGCGGGUGUG GGGCG           25

( 2 ) INFORMATION FOR SEQ ID NO:49:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:49:

CTACCTACGA TCTGACTAGC           20

( 2 ) INFORMATION FOR SEQ ID NO:50:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: N at position 2 and 4 is Biotin ( x i ) SEQUENCE DESCRIPTION: SEQ ID NO:50:

ANANAGGAAC TACATGAGAG TAAGC           25

( 2 ) INFORMATION FOR SEQ ID NO:51:

( i ) SEQUENCE CHARACTERISTICS:
        ( A ) LENGTH: 80 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:51:

```
CTACCTACGA TCTGACTAGC TACCCGCGAT GAGAGTAAGT TTATCCGTGT        50
ACTCTTAGTG GCTTACTCTC ATGTAGTTCC                              80
```

( 2 ) INFORMATION FOR SEQ ID NO:52:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:52:

```
CTACCTACGA TCTGACTAGC TACCCGCGTT GAGAGTAAGT TTATCCGTGT        50
ACTCTTAGTG GCTTACTCTC ATGTAGTTCC                              80
```

( 2 ) INFORMATION FOR SEQ ID NO:53:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:53:

```
CTACCTACGA TCTGACTAGC ACAGCATGAG AGATATAGCT TTATCCGTGA        50
CTCTCAGTGG GCTTACTCTC ATGTAGTTCC                              80
```

( 2 ) INFORMATION FOR SEQ ID NO:54:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:54:

```
CTACCTACGA TCTGACTAGC CAATTGCTGA AGGAAGCATT TATCCGTTCC        50
TCTTAGTGGT GCTTACTCTC ATGTAGTTCC                              80
```

( 2 ) INFORMATION FOR SEQ ID NO:55:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:55:

```
CTACCTACGA TCTGACTAGC CAACTGCTGA AGGAAGCATT TATCCGTTCC        50
TCTTAGTGGT GCTTACTCTC ATGTAGTTCC                              80
```

( 2 ) INFORMATION FOR SEQ ID NO:56:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

```
CTACCTACGA TCTGACTAGC AGGTCATGCG AGTATGCTTT ATCCGTAACC      50
TCTCAGTGGG CTTACTCTCA TGTAGTTCC                            79
```

( 2 ) INFORMATION FOR SEQ ID NO:57:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:57:

```
CTACCTACGA TCTGACTAGC CAATGAGTGT ACCACGTTTA TCCGTCCCTC      50
CTAGTGGCGT GCTTACTCTC ATGTAGTTCC                           80
```

( 2 ) INFORMATION FOR SEQ ID NO:58:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:58:

```
CTACCTACGA TCTGACTAGC CCCTGANGTG TNMAMKTTTG TWCCGTTYCT      50
CCTAGTGGCG TGCTTACTCT CATGTAGTTC C                         81
```

( 2 ) INFORMATION FOR SEQ ID NO:59:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:59:

```
CTACCTACGA TCTGACTAGC GGCCGTAAGC AACCTTTATC CGTAATCTCT      50
CAGTGGGGTA GCTTACTCTC ATGTAGTTCC                           80
```

( 2 ) INFORMATION FOR SEQ ID NO:60:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:60:

```
CTACCTACGA TCTGACTAGC GTGMGCGGGA TCTTTATYCG TTACTCTTAG    50
TGGGTCTCGG CTTACTCTCA TGTAGTTCC                           79
```

( 2 ) INFORMATION FOR SEQ ID NO:61:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:61:

```
CTACCTACGA TCTGACTAGC AAGGCGACTA CTTTATCCGT TTCTCTTAGT    50
GGGTATCCGG CTTACTCTCA TGTAGTTCC                           79
```

( 2 ) INFORMATION FOR SEQ ID NO:62:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:62:

```
CTACCTACGA TCTGACTAGC AATGGTCCAG CTTTATCCGT CTCTTTCAGT    50
GGGCGTCATT GCTTACTCTC ATGTAGTTCC                          80
```

( 2 ) INFORMATION FOR SEQ ID NO:63:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:63:

```
CTACCTACGA TCTGACTAGC CTACHGCCCA TTTATVCGTT CCTCCTAGTG    50
GTGGGCTGCT GCTTACTCTC ATGTAGTTCC                          80
```

( 2 ) INFORMATION FOR SEQ ID NO:64:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:64:

```
CTACCTACGA TCTGACTAGC RGCCGGGACA TTTATCCGTT ACTACTCAGT    50
GGGTGAACTG TCGCTTACTC TCATGTAGTT CC                       82
```

( 2 ) INFORMATION FOR SEQ ID NO:65:

( i ) SEQUENCE CHARACTERISTICS:
        ( A ) LENGTH: 80 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO:65:

CTACCTACGA TCTGACTAGC WCCGGAGTAC TTTATYCGTY CCTTCTAGTG    50

GGTACCCGTA GCTTACTCTC ATGTAGTTCC    80

( 2 ) INFORMATION FOR SEQ ID NO:66:

( i ) SEQUENCE CHARACTERISTICS:
      ( A ) LENGTH: 79 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:66:

CTACCTACGA TCTGACTAGC GGCCGGAGCT TTATCCGTTA CTCTCAGTGG    50

GTGACTGTCG CTTACTCTCA TGTAGTTCC    79

( 2 ) INFORMATION FOR SEQ ID NO:67:

( i ) SEQUENCE CHARACTERISTICS:
      ( A ) LENGTH: 80 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:67:

CTACCTACGA TCTGACTAGC GGCCGGAGCT TTATTCCGTT ACTCTCAGTG    50

GGTGACTGTC GCTTACTCTC ATGTAGTTCC    80

( 2 ) INFORMATION FOR SEQ ID NO:68:

( i ) SEQUENCE CHARACTERISTICS:
      ( A ) LENGTH: 79 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:68:

CTACCTACGA TCTGACTAGC CAAAGTTAAT TTATNCGTCC CTCCTAGTGG    50

TTAACAGCGG CTTACTCTCA TGTAGTTCC    79

( 2 ) INFORMATION FOR SEQ ID NO:69:

( i ) SEQUENCE CHARACTERISTICS:
      ( A ) LENGTH: 79 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:69:

CTACCTACGA TCTGACTAGC CAAAGTTAAT TTATCCGTCC CTCTCAGTGG    50

TTAACAGCGG CTTACTCTCA TGTAGTTCC    79

( 2 ) INFORMATION FOR SEQ ID NO:70:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:70:

```
CTACCTACGA TCTGACTAGC CAAGGTTAAT TTATYCGTCC CTCCCAGTGG        50
TTAACAGCGG CTTACTCTCA TGTAGTTCC                               79
```

( 2 ) INFORMATION FOR SEQ ID NO:71:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:71:

```
CTACCTACGA TCTGACTAGC GATGGGAGCT TTATCCGTTC ACTCTCAGTG        50
GGCTCCTCAG GCTTACTCTC ATGTAGTTCC                              80
```

( 2 ) INFORMATION FOR SEQ ID NO:72:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:72:

```
CTACCTACGA TCTGACTAGC GATGGGAGCT TTATCCGTTC ACTTTCAGTG        50
GGCTCCTCAT GCTTACTCTC ATGTAGTTCC                              80
```

( 2 ) INFORMATION FOR SEQ ID NO:73:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:73:

```
CTACCTACGA TCTGACTAGC CGAAGTTAAT TTATSCGTCC CTCCTAGTGG        50
YTTAACAGCG GCTTACTCTC ATGTAGTTCC                              80
```

( 2 ) INFORMATION FOR SEQ ID NO:74:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:74:

```
CTACCTACGA TCTGACTAGC CTTGCTCCAT TTATCCGTTT CTCCCAGTGG        50
```

TGGTTGCATG GCTTACTCTC ATGTAGTTCC                                80

( 2 ) INFORMATION FOR SEQ ID NO:75:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:75:

CTACCTACGA TCTGACTAGC CTACGCGCTT TATCCGTTTC TCCCAGTGGG          50

CGGGCGTTCG CTTACTCTCA TGTAGTTCC                                 79

( 2 ) INFORMATION FOR SEQ ID NO:76:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:76:

CTACCTACGA TCTGACTAGC GTVSSGCTTT ATCCGTTNCT CCCAGTGGGC          50

GGGCRTTCGC TTACTCTCAT GTAGTTCC                                  78

( 2 ) INFORMATION FOR SEQ ID NO:77:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:77:

CTACCTACGA TCTGACTAGC GGCTTTATCC GTAACCTCTT AGTGGGCCGC          50

NCGCTTCACA GCTTACTCTC ATGTAGTTCC                                80

( 2 ) INFORMATION FOR SEQ ID NO:78:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:78:

CTACCTACGA TCTGACTAGC ATGGGAGAAC ACTTAGCCTT CATCCGTTCC          50

TCCTAGTGGG GCTTACTCTC ATGTAGTTCC                                80

( 2 ) INFORMATION FOR SEQ ID NO:79:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:79:

CTACCTACGA TCTGACTAGC CGCGCGTACG AGCACCTTCA TCCGTCCCTC        50

CTAGTGGGGT GCTTACTCTC ATGTAGTTCC        80

( 2 ) INFORMATION FOR SEQ ID NO:80:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:80:

CTACCTACGA TCTGACTAGC GGCCGTAASC AAGCCTTYWT CCGTMACCTA        50

CTYAGTGGGG KRGCTTACTC TCATGTAGTT CC        82

( 2 ) INFORMATION FOR SEQ ID NO:81:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:81:

CTACCTACGA TCTGACTAGC NNNNNNNNCT CTTTCATCCG TACCTCCCAG        50

TGGAGAACGC GCTTACTCTC ATGTAGTTCC        80

( 2 ) INFORMATION FOR SEQ ID NO:82:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:82:

CTACCTACGA TCTGACTAGC ACCGGAGTAC TTCATCCGTC CCTTCTAGTG        50

GGTACCCGTA GCTTACTCTC ATGTAGTTCC        80

( 2 ) INFORMATION FOR SEQ ID NO:83:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:83:

CTACCTACGA TCTGACTAGC TCCGGAGTAC TTCATCCGTY CCTTCTAGTG        50

GGTACCCGTA GCTTACTCTC ATGTAGTTCC        80

( 2 ) INFORMATION FOR SEQ ID NO:84:

( i ) SEQUENCE CHARACTERISTICS:

(A) LENGTH: 80 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:84:

CTACCTACGA TCTGACTAGC AGGGATGTTC ATCCGTTCCT CTCAGTGGCA       50

TCCCGTGGCT GCTTACTCTC ATGTAGTTCC                            80

(2) INFORMATION FOR SEQ ID NO:85:

(i) SEQUENCE CHARACTERISTICS:
         (A) LENGTH: 80 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:85:

CTACCTACGA TCTGACTAGC NNNNGGTTCA TCCGTTCCTT CTAGTGGCCA       50

CCTGGATGCA GCTTACTCTC ATGTAGTTCC                            80

(2) INFORMATION FOR SEQ ID NO:86:

(i) SEQUENCE CHARACTERISTICS:
         (A) LENGTH: 80 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:86:

CTACCTACGA TCTGACTAGC TGGCATTCAT CCGTCTCTCC TAGTGGTGCC       50

TTGTCCCCCA GCTTACTCTC ATGTAGTTCC                            80

(2) INFORMATION FOR SEQ ID NO:87:

(i) SEQUENCE CHARACTERISTICS:
         (A) LENGTH: 80 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:87:

CTACCTACGA TCTGACTAGC CCTTCATCCG TTACTCTTAG TGGGGGCTTG       50

CGATTCGAGT GCTTACTCTC ATGTAGTTCC                            80

(2) INFORMATION FOR SEQ ID NO:88:

(i) SEQUENCE CHARACTERISTICS:
         (A) LENGTH: 80 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:88:

CTACCTACGA TCTGACTAGC TGCTGGACAA TTGATCCGTT ACTCTTAGTG       50

GTTGTGTGCT GCTTACTCTC ATGTAGTTCC                            80

( 2 ) INFORMATION FOR SEQ ID NO:89:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:89:

```
CTACCTACGA TCTGACTAGC ACGGGTGAGT TGATCCGTTA CTCTTAGTGG        50
TGAACCTTGT GCTTACTCTC ATGTAGTTCC                              80
```

( 2 ) INFORMATION FOR SEQ ID NO:90:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:90:

```
CTACCTACGA TCTGACTAGC ACGGGTGAGT TGATCCGTCA CTCTTAGTGG        50
TGAACCTTGT GCTTACTCTC ATGTAGTTCC                              80
```

( 2 ) INFORMATION FOR SEQ ID NO:91:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:91:

```
CTACCTACGA TCTGACTAGC ACAGGTGAGT TGATCCGTTA CTCTTAGTGG        50
TGAACCTTGT GCTTACTCTC ATGTAGTTCC                              80
```

( 2 ) INFORMATION FOR SEQ ID NO:92:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:92:

```
CTACCTACGA TCTGACTAGC ACTGGTGAKT TGATCCGTCA CTCTTAGTGG        50
TGAWCCTTGT GCTTACTCTC ATGTAGTTCC                              80
```

( 2 ) INFORMATION FOR SEQ ID NO:93:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:93:

CACGTTTATC CGTCCCTCCT AGTGGCGTG                                    29

( 2 ) INFORMATION FOR SEQ ID NO:94:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:94:

GGGGCACGTT TATCCGTCCC TCCTAGTGGC GTGCCCC                            37

( 2 ) INFORMATION FOR SEQ ID NO:95:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:95:

CTACCTACGA TCTGACTAGC GGCGTTTTAC TTACTGGTCT TAGACCGGAG              50

AGACACAGTC GCTTACTCTC ATGTAGTTCC                                   80

( 2 ) INFORMATION FOR SEQ ID NO:96:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:96:

CTACCTACGA TCTGACTAGC GGCGTTTTAC GTGTACKGGT CATGTGAGRC              50

SGGAGAGACA CRGTKGCTTA CTCTCATGTA GTTCC                              85

( 2 ) INFORMATION FOR SEQ ID NO:97:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:97:

CTACCTACGA TCTGACTAGC GATGGGNGGG GGACGTGCTG ATTTCCCACT              50

TCATATTTCG TGCTTACTCT CATGTAGTTC C                                  81

( 2 ) INFORMATION FOR SEQ ID NO:98:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:98:

CTACCTACGA TCTGACTAGC GAGGGTGTGG GACGTGCTGA TTTCCCACTT    50

CATATTTCGT GCTTACTCTC ATGTAGTTCC    80

( 2 ) INFORMATION FOR SEQ ID NO:99:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:99:

CTACCTACGA TCTGACTAGC CTGGGKKTCC CGCGGAKCKG TTACCAGTTA    50

TGGGGCAAGG CTTACTCTCA TGTAGTTCC    79

( 2 ) INFORMATION FOR SEQ ID NO:100:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:100:

CTACCTACGA TCTGACTAGC CTGGGGGTSC CGCGGAGCGT GTTACCAGTT    50

ATGGGGCAAT GCTTACTCTC ATGTAGTTCC    80

( 2 ) INFORMATION FOR SEQ ID NO:101:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:101:

CTACCTACGA TCTGACTAGC CTGGGGGTCC CGCGTAGCGT GTTACCAGTT    50

ATGGGGCAAT GCTTACTCTC ATGTAGTTCC    80

( 2 ) INFORMATION FOR SEQ ID NO:102:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:102:

CTACCTACGA TCTGACTAGC CCTACCGTCG KCGCGGTTAA GGAAACTACB    50

GCCTTTTACB GCTTACTCTC ATGTAGTTCC    80

( 2 ) INFORMATION FOR SEQ ID NO:103:

( i ) SEQUENCE CHARACTERISTICS:
        ( A ) LENGTH: 80 base pairs (B) TYPE: nucleic acid
    (C) STRANDEDNESS: single
    (D) TOPOLOGY: linear ( i i ) MOLECULE TYPE: DNA ( x i ) SEQUENCE DESCRIPTION: SEQ ID NO:103:

CTACCTACGA TCTGACTAGC ACCGCTAGTT TCGAGGTTGG ACGTGTTTGC    50

CGTGTCGATT GCTTACTCTC ATGTAGTTCC    80

( 2 ) INFORMATION FOR SEQ ID NO:104:

( i ) SEQUENCE CHARACTERISTICS:
        (A) LENGTH: 80 base pairs
        (B) TYPE: nucleic acid
        (C) STRANDEDNESS: single
        (D) TOPOLOGY: linear ( i i ) MOLECULE TYPE: DNA ( x i ) SEQUENCE DESCRIPTION: SEQ ID NO:104:

CTACCTACGA TCTGACTAGC ACCGCTAGTT TCGAGGTTGG ACGTGTTTGC    50

CGTGTCGATT GCTTACTCTC ATGTAGTTCC    80

( 2 ) INFORMATION FOR SEQ ID NO:105:

( i ) SEQUENCE CHARACTERISTICS:
        (A) LENGTH: 80 base pairs
        (B) TYPE: nucleic acid
        (C) STRANDEDNESS: single
        (D) TOPOLOGY: linear ( i i ) MOLECULE TYPE: DNA ( x i ) SEQUENCE DESCRIPTION: SEQ ID NO:105:

CTACCTACGA TCTGACTAGC GTTGGACGGT TACGTTTCCT CATGGCAACC    50

CAGCTAGATC GCTTACTCTC ATGTAGTTCC    80

( 2 ) INFORMATION FOR SEQ ID NO:106:

( i ) SEQUENCE CHARACTERISTICS:
        (A) LENGTH: 78 base pairs
        (B) TYPE: nucleic acid
        (C) STRANDEDNESS: single
        (D) TOPOLOGY: linear ( i i ) MOLECULE TYPE: DNA ( x i ) SEQUENCE DESCRIPTION: SEQ ID NO:106:

CTACCTACGA TCTGACTAGC TTTCCCTCGA CGGGTGCCCA CTGCGGCATG    50

GGTTAAGAGC TTACTCTCAT GTAGTTCC    78

( 2 ) INFORMATION FOR SEQ ID NO:107:

( i ) SEQUENCE CHARACTERISTICS:
        (A) LENGTH: 79 base pairs
        (B) TYPE: nucleic acid
        (C) STRANDEDNESS: single
        (D) TOPOLOGY: linear ( i i ) MOLECULE TYPE: DNA ( x i ) SEQUENCE DESCRIPTION: SEQ ID NO:107:

CTACCTACGA TCTGACTAGC TGGGGCAGCT TTGCGNGGGT CCTACGTTTT    50

ACDTTTGCCG CTTACTCTCA TGTAGTTCC    79

( 2 ) INFORMATION FOR SEQ ID NO:108:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:108:

```
CTACCTACGA  TCTGACTAGC  NNCGTCCTTC  CAGTGGTGGA  GTACCACCCG     50
TCCGGCACTT  GCTTACTCTC  ATGTAGTTCC                             80
```

( 2 ) INFORMATION FOR SEQ ID NO:109:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:109:

```
CTACCTACGA  TCTGACTAGC  CGCGGGTGAT  CGGATTRCCC  TGCATCTCCR     50
CCTGATTCTT  GCTTACTCTC  ATGTAGTTCC                             80
```

( 2 ) INFORMATION FOR SEQ ID NO:110:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:110:

```
CTACCTACGA  TCTGACTAGC  GATNGCGTTT  CGATACTGCT  TCTGCGGAGT     50
CACACAGCTC  GCTTACTCTC  ATGTAGTTCC                             80
```

( 2 ) INFORMATION FOR SEQ ID NO:111:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:111:

```
CTACCTACGA  TCTGACTAGC  AGGCGGGTNC  CCTCTGGCGG  AACACTTTGC     50
TGTTGTCCTG  CTTACTCTCA  TGTAGTTCC                              79
```

( 2 ) INFORMATION FOR SEQ ID NO:112:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:112:

```
CTACCTACGA TCTGACTAGC NNNNNNNNNN NNNNNNNNNN NNNNNNNNNN       50
NNNNNNNNNN GCTTACTCTC ATGTAGTTCC                             80
```